(12) United States Patent
Heil et al.

(10) Patent No.: US 8,697,435 B2
(45) Date of Patent: Apr. 15, 2014

(54) INTEGRATED SAMPLE PREPARATION AND ANALYTE DETECTION

(75) Inventors: James R. Heil, Denver, CO (US);
Michael J. Lochhead, Boulder, CO (US); Kevin D. Moll, Boulder, CO (US);
Christopher J. Myatt, Boulder, CO (US)

(73) Assignee: MBio Diagnostics, Inc., Boulder, CO (US)

( * ) Notice: Subject to any disclaimer, the term of this patent is extended or adjusted under 35 U.S.C. 154(b) by 559 days.

(21) Appl. No.: 12/871,402

(22) Filed: Aug. 30, 2010

(65) Prior Publication Data

US 2011/0065209 A1 Mar. 17, 2011

Related U.S. Application Data

(60) Provisional application No. 61/238,376, filed on Aug. 31, 2009.

(51) Int. Cl.
*C12M 1/34* (2006.01)
*G01N 33/543* (2006.01)

(52) U.S. Cl.
CPC ....... *G01N 33/54326* (2013.01); *Y10S 435/808* (2013.01); *Y10S 436/805* (2013.01); *Y10S 436/806* (2013.01)
USPC ............ 435/288.7; 422/414; 422/82.11; 435/287.2; 435/288.5; 435/808; 436/526; 436/805; 436/806

(58) Field of Classification Search
CPC .......... G01N 21/648; G01N 33/54326; G01N 33/54373; B01L 3/50273
See application file for complete search history.

(56) References Cited

U.S. PATENT DOCUMENTS

| 2,885,366 A | 5/1959 | Iler |
| 2,913,419 A | 11/1959 | Alexander |

(Continued)

FOREIGN PATENT DOCUMENTS

| WO | 0114591 A1 | 3/2001 |
| WO | 0234951 A2 | 5/2002 |

(Continued)

OTHER PUBLICATIONS

Bally, M., et al., "Particle Flow Assays for Fluorescent Protein Microarray Applications", "Biosensors and Bioelectronics", 2009, pp. 1195-1200, vol. 24, Publisher: Elsevier B.V.

(Continued)

*Primary Examiner* — Chris L Chin
(74) *Attorney, Agent, or Firm* — Lathrop & Gage LLP

(57) ABSTRACT

A system for sample preparation and analyte detection includes a cartridge, with a fluidic channel, a waveguide, and a capture spot. The system further includes a force field generator, an imaging system, and a fluid, which includes a sample potentially containing a target analyte, first type particles, which include binding moieties specific for the target analyte and are responsive to a force field, and second type particles, which include binding moieties specific for the target analyte and are capable of generating a signal. When the sample contains the target analyte, specific binding interactions between the target analyte and binding moieties link first and second type particles via the target analyte to form multiple-particle complex capturable at a capture spot. The force field allows manipulation of the particles and multiple-particle complex such that the detected signal from the second type particles is indicative of the target analyte within the sample.

22 Claims, 15 Drawing Sheets

(56) References Cited

U.S. PATENT DOCUMENTS

| | | |
|---|---|---|
| 3,926,659 A | 12/1975 | Bernhard et al. |
| 3,933,997 A | 1/1976 | Hersh et al. |
| 3,945,862 A | 3/1976 | Lee et al. |
| 3,970,518 A | 7/1976 | Giaever |
| 4,082,905 A | 4/1978 | Stephan et al. |
| 4,115,535 A | 9/1978 | Giaever |
| 4,124,385 A | 11/1978 | O'Horo |
| 4,124,735 A | 11/1978 | O'Horo |
| 4,126,437 A | 11/1978 | O'Horo |
| 4,230,685 A | 10/1980 | Senyei et al. |
| 4,233,169 A | 11/1980 | Beall et al. |
| 4,280,918 A | 7/1981 | Homola et al. |
| 4,297,337 A | 10/1981 | Mansfield et al. |
| 4,309,459 A | 1/1982 | Tokuoka |
| 4,336,310 A | 6/1982 | Okuyama et al. |
| 4,360,441 A | 11/1982 | Borrelli et al. |
| 4,395,271 A | 7/1983 | Beall et al. |
| 4,554,088 A | 11/1985 | Whitehead et al. |
| 4,564,537 A | 1/1986 | Austin et al. |
| 4,628,037 A | 12/1986 | Chagnon et al. |
| 4,672,040 A | 6/1987 | Josephson |
| 4,683,202 A | 7/1987 | Mullis |
| 4,695,392 A | 9/1987 | Whitehead et al. |
| 4,695,393 A | 9/1987 | Chagnon et al. |
| 4,698,302 A | 10/1987 | Whitehead et al. |
| 4,699,717 A | 10/1987 | Riesner et al. |
| 4,731,337 A | 3/1988 | Luotola et al. |
| 4,751,211 A | 6/1988 | Fleming |
| 4,767,670 A | 8/1988 | Cox et al. |
| 4,777,145 A * | 10/1988 | Luotola et al. ............... 436/526 |
| 4,804,561 A | 2/1989 | Tanioka et al. |
| 4,824,712 A | 4/1989 | Falleroni et al. |
| 4,910,148 A | 3/1990 | Sorensen et al. |
| 4,920,061 A * | 4/1990 | Poynton et al. ............... 436/526 |
| 5,039,559 A | 8/1991 | Sang et al. |
| 5,055,194 A | 10/1991 | Goetz et al. |
| 5,057,426 A | 10/1991 | Henco et al. |
| 5,075,430 A | 12/1991 | Little |
| 5,076,950 A | 12/1991 | Ullman et al. |
| 5,145,784 A * | 9/1992 | Cox et al. ............... 436/526 |
| 5,155,018 A | 10/1992 | Gillespie et al. |
| 5,206,568 A | 4/1993 | Bjornson et al. |
| 5,210,015 A | 5/1993 | Gelfand |
| 5,217,804 A | 6/1993 | James et al. |
| 5,234,809 A | 8/1993 | Boom et al. |
| 5,236,623 A | 8/1993 | Chevallier |
| 5,279,936 A | 1/1994 | Vorpahl |
| 5,312,485 A | 5/1994 | Wason et al. |
| 5,316,699 A | 5/1994 | Ritter et al. |
| 5,340,393 A | 8/1994 | Jacobson |
| 5,346,994 A | 9/1994 | Chomczynski |
| 5,352,645 A | 10/1994 | Schwartz |
| 5,368,933 A | 11/1994 | Aoki et al. |
| 5,389,482 A | 2/1995 | Okano et al. |
| 5,395,498 A | 3/1995 | Gombinsky et al. |
| 5,438,127 A | 8/1995 | Woodard et al. |
| 5,443,791 A | 8/1995 | Cathcart et al. |
| 5,445,971 A | 8/1995 | Rohr |
| 5,458,813 A | 10/1995 | Palladino |
| 5,470,660 A | 11/1995 | Misawa et al. |
| 5,486,335 A | 1/1996 | Wilding et al. |
| 5,487,972 A | 1/1996 | Gelfand et al. |
| 5,503,816 A | 4/1996 | Woodard et al. |
| 5,512,332 A | 4/1996 | Liberti et al. |
| 5,512,405 A | 4/1996 | Misawa et al. |
| 5,512,439 A | 4/1996 | Hornes et al. |
| 5,520,899 A | 5/1996 | Woodard et al. |
| 5,578,238 A | 11/1996 | Weiss et al. |
| 5,582,988 A | 12/1996 | Backus et al. |
| 5,597,531 A | 1/1997 | Liberti et al. |
| 5,599,627 A | 2/1997 | Aoki et al. |
| 5,605,662 A | 2/1997 | Heller et al. |
| 5,610,274 A | 3/1997 | Wong |
| 5,648,170 A | 7/1997 | Okano et al. |
| 5,658,548 A | 8/1997 | Padhye et al. |
| 5,660,984 A | 8/1997 | Davis et al. |
| 5,662,824 A | 9/1997 | Sang et al. |
| 5,665,554 A | 9/1997 | Reeve et al. |
| 5,681,946 A | 10/1997 | Reeve |
| 5,683,875 A | 11/1997 | Lichtenwalter |
| 5,693,502 A | 12/1997 | Gold et al. |
| 5,693,785 A | 12/1997 | Woodard et al. |
| 5,698,271 A | 12/1997 | Liberti et al. |
| 5,698,397 A | 12/1997 | Zarling et al. |
| 5,705,137 A | 1/1998 | Goerl et al. |
| 5,734,020 A | 3/1998 | Wong |
| 5,741,714 A | 4/1998 | Liberti |
| 5,747,663 A | 5/1998 | Colpan et al. |
| 5,763,173 A | 6/1998 | Gold et al. |
| 5,783,686 A | 7/1998 | Gonzalez |
| 5,804,375 A | 9/1998 | Gelfand et al. |
| 5,807,675 A | 9/1998 | Davalian et al. |
| 5,898,071 A | 4/1999 | Hawkins |
| 5,904,848 A | 5/1999 | Wong et al. |
| 5,925,573 A | 7/1999 | Colin et al. |
| 5,928,958 A | 7/1999 | Pilgrimm |
| 5,945,525 A | 8/1999 | Uematsu et al. |
| 5,962,218 A | 10/1999 | Leland et al. |
| 5,972,721 A | 10/1999 | Bruno et al. |
| 5,973,138 A | 10/1999 | Collis |
| 5,981,180 A | 11/1999 | Chandler et al. |
| 5,990,301 A | 11/1999 | Colpan et al. |
| 5,990,479 A | 11/1999 | Weiss et al. |
| 6,013,531 A | 1/2000 | Wang et al. |
| 6,027,945 A | 2/2000 | Smith et al. |
| 6,136,083 A | 10/2000 | Schmidt et al. |
| 6,136,549 A | 10/2000 | Feistel |
| 6,180,415 B1 | 1/2001 | Schultz et al. |
| 6,184,042 B1 | 2/2001 | Neumann et al. |
| 6,214,560 B1 | 4/2001 | Yguerabide et al. |
| 6,255,477 B1 | 7/2001 | Kleiber et al. |
| 6,274,386 B1 | 8/2001 | Harttig |
| 6,296,937 B2 | 10/2001 | Pryor et al. |
| 6,325,973 B1 | 12/2001 | Leland et al. |
| 6,348,318 B1 | 2/2002 | Valkirs |
| 6,368,800 B1 | 4/2002 | Smith et al. |
| 6,406,913 B1 | 6/2002 | Ullman et al. |
| 6,479,302 B1 | 11/2002 | Dremel |
| 6,696,304 B1 | 2/2004 | Davies |
| 6,714,299 B2 | 3/2004 | Peterson et al. |
| 6,815,173 B1 | 11/2004 | Pope et al. |
| 6,870,045 B2 | 3/2005 | Yang et al. |
| 6,958,865 B1 | 10/2005 | Quake et al. |
| 6,984,491 B2 | 1/2006 | Mirkin et al. |
| 7,138,269 B2 | 11/2006 | Blankenstein |
| 7,173,124 B2 | 2/2007 | Deggerdal et al. |
| 7,248,413 B2 | 7/2007 | Quake et al. |
| 7,314,763 B2 | 1/2008 | Song et al. |
| 7,341,841 B2 | 3/2008 | Metzger et al. |
| 7,390,675 B2 | 6/2008 | Feistel |
| 7,432,105 B2 | 10/2008 | Song et al. |
| 7,504,262 B2 | 3/2009 | Fox |
| 7,547,557 B2 | 6/2009 | LaBorde et al. |
| 7,727,473 B2 | 6/2010 | Ching et al. |
| 7,749,775 B2 | 7/2010 | Maher et al. |
| 2002/0177127 A1 | 11/2002 | Yang et al. |
| 2004/0018611 A1 | 1/2004 | Ward et al. |
| 2006/0068412 A1 | 3/2006 | Tang |
| 2007/0031283 A1 | 2/2007 | Davis et al. |
| 2007/0105163 A1 | 5/2007 | Grate et al. |
| 2007/0166835 A1 | 7/2007 | Bobrow et al. |
| 2008/0160634 A1 | 7/2008 | Su et al. |
| 2008/0241909 A1 | 10/2008 | Jung et al. |
| 2009/0170212 A1* | 7/2009 | Van Der Wijk et al. ...... 436/149 |
| 2010/0009456 A1 | 1/2010 | Prins et al. |

FOREIGN PATENT DOCUMENTS

| | | |
|---|---|---|
| WO | WO02/42498 | 5/2002 |
| WO | 2007002579 A2 | 1/2007 |

(56) References Cited

FOREIGN PATENT DOCUMENTS

WO       2008094198 A2       8/2008

OTHER PUBLICATIONS

Bally, Marta, "A Microarray Assay with Fluorescent Microparticles", "European Cells and Materials", 2007, p. 40, vol. 14, No. Supp. 3, Publisher: Institute for Biomedical Engineering, Published in: CH.
Barbee, K.D., et al., "Electric Field Directed Assembly of High-Density Microbead Arrays", "Lab on a Chip", Nov. 21, 2009, pp. 3268-3274, vol. 9, No. 22, Publisher: The Royal Society of Chemistry.
Beaudet, L., et al., "Homogeneous Assays for Single-Nucleotide Polymorphism Typing Using AlphaScreen", "Genome Research", 2001, pp. 600-608, vol. 11, Publisher: Cold Spring Harbor Laboratory Press.
Mehta, P., et al., "The Diagnostics Innovation Map: Medical Diagnostics for the Unmet Needs of the Developing World", "BIO Ventures for Global Health", 2010, p. 88.
Boguslawski, S.J., et al., "Characterization of Monoclonal Antibody to DNA RNA and its Application to Immunodetection of Hybrids", "Journal of Immunological Methods", 1986, pp. 123-130, vol. 89, Publisher: Elsevier Science Publishers B.V.
Bonarius, H.P.J., et al., "Monitoring the T-Cell Receptor Repertoire at Single-Clone Resolution", "PloS One", Dec. 2006, p. 10 vol. 1, No. e55, Publisher: www.plosone.org.
Boom, R., et al., "Rapid and Simple Method for Purification of Nucleic Acids", "Journal of Clinical Microbiology", Mar. 1990, pp. 495-503, Publisher: American Society for Microbiology.
Brandt, O., et al., "Peptide Nucleic Acids on Microarrays and other Biosensors", "Trends in Biotechnology", Dec. 2004, pp. 617-622, vol. 22, No. 12, Publisher: Elsevier Ltd.
Breslauer, D.N., et al, "Mobile Phone Based Clinical Microscopy for Global Health Applications", "PloS One", Jul. 2009, vol. 4, No. 7, Publisher: www.plosone.com.
Cao, W., et al., "Chitosan as a Polymer for pH-Induced DNA Capture in a Totally Aqueous System", "Analytical Chemistry", Oct. 15, 2006, pp. 7222-7228, vol. 78, No. 20, Publisher: American Chemical Society.
Carlson, M.A., et al., "An Automated, Handheld Biosensor for Aflatoxin", "Biosensors and Bioelectronics", 2000, pp. 841-848, vol. 14, Publisher: Elsevier Science S.A.
Carter, D.J., et al., "Lateral Flow Microarrays: A Novel Platform for Rapid Nucleic Acid Detection Based on Miniaturized Lateral Flow Chromatography", "Nucleic Acids Research", May 3, 2007, pp. e74, vol. 35, No. 10, Publisher: The Creative Commons Attribution.
Chen, J., et al, "Detection of *Salmonella* and Simultaneous Detection of *Salmonella* and Shiga-Like Toxin-Producing *Escherichia coli* Using the Magnetic Capture Hybridization Polymerase Chain Reaction", "Letters in Applied Microbiology", 2001, pp. 711, vol. 32, Publisher: The Society for Applied Microbiology.
Christodoulides, N., et al., "Application of Microchip Assay System for the Measurement of C-Reactive Protein in Human Saliva", "Lab on a Chip", 2005, pp. 261-269, vol. 5, Publisher: The Royal Society of Chemistry.
Crowe, Suzanne, "Review of CD4 Technologies", "Presentation", 2005, p. 55 Publisher: Forum for Collaborative HIV Research.
Dandy, D.S., et al., "Array Feature Size Influences Nucleic Acid Surface Capture in DNA Microarrays", "PNAS", May 15, 2007, pp. 8223-8228, vol. 104, No. 20, Publisher: The National Academy of Sciences of the USA.
Davis, K.A., et al., "Determination of CD4 Antigen Density on Cells: Role of Antibody Valency, Avidity, Clones, and Conjugation", "Cytometry", 1998, pp. 197-205, vol. 33, Publisher: Wiley-Liss, Inc.
Dimov, I.K., et al., "Integrated Microfluidic tmRNA Purification and Real-Time NASBA Device for Molecular Diagnostics", "Lab on a Chip", 2008, pp. 2071-2078, vol. 8, Publisher: The Royal Society of Chemistry.
Dineva, M.A., et al., "Sample Preparation: A Challenge in the Development of Point-of-Care Nucleic Acid-Based Assays for Resource-Limited Settings", "The Analyst", 2007, pp. 1193-1199, vol. 132, Publisher: The Royal Society of Chemistry.
Dundas, N., et al., "Comparison of Automated Nucleic Acid Extraction Methods with Manual Extraction", "Journal of Molecular Diagnostics", Jul. 2008, pp. 311-316, vol. 10, No. 4, Publisher: The American Society for Investigative Pathology and the Association for Molecular Pathology.
Edelstein, R.L., et al., "The BARC Biosensor Applied to the Detection of Biological Warfare Agents", "Biosensors and Bioelectronics", 2000, pp. 805-813, vol. 14, Publisher: Elsevier Science S.A.
Erickson, D., et al., "Integrated Microfluidic Devices", "Analytica Chimica Acta", 2004, pp. 11-26, vol. 507, Publisher: Elsevier B.V.
Espicom, "POC Diagnostics: Players, Products & Future Market Prospects", Nov. 2009, Publisher: Espicom Business Intelligence.
Fahy, E., et al., "Design and Synthesis of Polyacrylamide-Based Oligonucleotide Supports for use in Nucleic Acid Diagnostics", "Nucleic Acids Research", 1993, pp. 1819-1826, vol. 21, No. 8, Publisher: Oxford University Press.
Lee, W.G., et al., "Nano/Microfluidics for Diagnosis of Infectious Diseases in Developing Countries", "Advanced Drug Delivery Reviews", 2010, pp. 449-457, vol. 62, Publisher: Elsevier B. V.
Lee, W.C., et al., "An Integrated Microfluidic System Using Magnetic Beads for Virus Detection", "Diagnostic Microbiology and Infectious Disease", 2008, pp. 51-58, vol. 60, Publisher: Elsevier, Inc.
Li, X., et al., "CD4 and CD8 Enumeration for HIV Monitoring in Resource-Constrained Settings", "Cytometry Part B (Clinical Cytometry)", 2009, pp. 118-126, vol. 76B, Publisher: Clinical Cytometry Society.
Lipman, N.S., et al., "Monoclonal Versus Polyclonal Antibodies: Distinguishing Characteristics, Applications, and Information Resources", "ILAR Journal", 2005, pp. 258-268, vol. 46, No. 3, Publisher: National Academy of Sciences.
Lo, A.C.T., et al., "Chapter 22: Review of Molecular Techniques for Sexually Transmitted Diseases Diagnosis", "Advanced Techniques in Diagnostic Microbiology, Part II", 2006, pp. 353-386.
Mabey, D., et al., "Diagnostic for the Developing World", "Nature Reviews Microbiology", Mar. 2004, pp. 231-240, vol. 2.
Malic, L., et al., "Current State of Intellectual Property in Microfluidic Nucleic Acid Analysis", "Recent Patents on Engineering", 2007, pp. 71-88, vol. 1, Publisher: Bentham Science Publishers, Ltd.
Miller, M.M., et al., "A DNA Array Sensor Utilizing Magnetic Microbeads and Magnetoelectronic Detection", "Journal of Magnetism and Magnetic Materials", 2001, pp. 138-144, vol. 225, Publisher: Elsevier Science B.V.
Morozov, V.N., et al., "Three Minutes-Long Electrophoretically Assisted Zeptomolar Microfluidic Immunoassay with Magnetic-Beads Detection", "Journal of American Chemical Society", 2007, pp. 12628, vol. 129, Publisher: American Chemical Society.
Muir, P., et al., "Rapid Diagnosis of Enterovirus Infection by Magnetic Bead Extraction and Polymerase Chain Reaction Detection of Enterovirus RNA in Clinical Specimens", "Journal of Clinical Microbiology", Jan. 1993, pp. 31-38, vol. 31, No. 1, Publisher: American Society for Microbiology.
Nichkova, M., et al., "Multiplexed Immunoassays for Proteins Using Magnetic Luminescent Nanoparticles for Internal Calibration", "Analytical Biochemistry", 2007, pp. 34-40, vol. 369, Publisher: Elsevier, Inc.
Niemeyer, C.M., et al., "Oligonucleotide-Directed Self-Assembly of Proteins: Semisynthetic DNA—Streptavidin Hybrid Molecules as Connectors for the Generation of Macroscopic Arrays and the Construction of Supramolecular Bioconjugates", "Nucleic Acids Research", 1994, pp. 5530-5539, vol. 22, No. 25, Publisher: Oxford University Press.
Olsvik, O., et al., "Magnetic Separation Techniques in Diagnostic Microbiology", "Clinical Microbiology Reviews", Jan. 1994, pp. 43-54, vol. 7, No. 1, Publisher: American Society for Microbiology.
Osterfeld, S.J., et al., "Multiplex Protein Assays Based on Real-Time Magnetic Nanotag Sensing", "PNAS", , pp. 20637-20640, vol. 105, No. 52, Publisher: The National Academy of Sciences of the USA.

(56) References Cited

OTHER PUBLICATIONS

Parsa, H., et al., "Effect of Volume- and Time-Based Constraints on Capture of Analytes in Microfluidic Heterogeneous Immunoassays", "Lab on a Chip", 2008, pp. 2062-2070, vol. 8, Publisher: The Royal Society of Chemistry.

Robinson, W.H., et al., "Autoantigen Microarrays for Multiplex Characterization of Autoantibody Responses", "Nature Medicine", Mar. 2002, pp. 295-301, vol. 8, No. 3, Publisher: Nature Publishing Group.

Scriba, T.J., et al., "HIV-1 Specific CD4+ T Lymphocyte Turnover and Activation Increase upon Viral Rebound", "The Journal of Clinical Investigation", Feb. 2005, vol. 115, No. 2.

Stimpson, D.I., et al., "Real-Time Detection of DNA Hybridization and Melting on Oligonucleotide Arrays by using Optical Wave Guides", "Proc. Natl. Acad Sci.", Jul. 1995, pp. 6379-6383, vol. 92.

Wu, Alan, "A Selected History and Future of Immunoassay Development and Applications in Clinical Chemistry", "Clinica Chimica Acta", 2006, pp. 119-124, vol. 369, Publisher: Elsevier B.V.

Young, Lee W., "International Search Report and Written Opinion dated Dec. 23, 2010 in PCT Application No. PCT/US10/47145", , Published in: US.

Feldhaus, M.J., et al., "Oligonucleotide-Conjugated Beads for Transdominant Genetic Experiments", "Nucleic Acids Research", 2000, pp. 534-543, vol. 28, No. 2, Publisher: Oxford University Press.

Fox, J.D., et al., "Development and Evaluation of Nucleic Acid Sequence Based Amplification (NASBA) for Diagnosis of Enterovirus Infections using the NucliSens Basic Kit", "Journal of Clinical Virology", 2002, pp. 117-130, vol. 24, Publisher: Elsevier Science B.V.

Gorkin, R., et al., "Centrifugal Microfluidics for Biomedical Applications", "Lab on a Chip", 2010, pp. 1758-1773, vol. 10, Publisher: The Royal Society of Chemistry.

Granade, T.C., et al., "Rapid Detection and Differentiation of Antibodies to HIV-1 and HIV-2 Using Multivalent Antigens and Magnetic Immunochromatography Testing", "Clinical and Vaccine Immunology", Jun. 2010, pp. 1034-1039, vol. 17, No. 6, Publisher: American Society for Microbiology.

Hagan, K.A., et al., "Microchip-Based Solid-Phase Purification of RNA from Biological Samples", "Analytical Chemistry", Nov. 15, 2008, pp. 8453-8460, vol. 80, No. 22, Publisher: American Chemical Society.

Hagan, K.A., et al., "Chitosan-Coated Silica as a Solid Phase for RNA Purification in a Microfluidic Device", "Analytical Chemistry", Jul. 1, 2009, pp. 5249-5256, vol. 81, No. 13, Publisher: American Chemical Society.

Hartmann, M., et al., "Protein Microarrays for Diagnostic Assays", "Analytical and Bioanalytical Chemistry", 2009, pp. 1407-1416, vol. 393, Publisher: Springer-Verlag.

Hashida, S., et al., "Measurement of Human Immunodeficiency Virus Type 1 p24 in Serum by an Ultrasensitive Enzyme Immunoassay, the Two-Site Immune Complex Transfer Enzyme Immunoassay", "Journal of Clinical Microbiology", Feb. 1995, pp. 298-303, vol. 33, No. 2, Publisher: American Society for Microbiology.

Hashsham, S.A., et al., "Potential of DNA Microarrays for Developing Parallel Detection Tools (PDTs) for Microorganisms Relevant to Biodefense and Related Research Needs", "Biosensors and Bioelectronics", 2004, pp. 668-683, vol. 20, Publisher: Elsevier B.V.

Ho, A., et al., "Attomoles Quantitative Chemiluminescence for Molecular Diagnostics", "American Biotechnology Laboratory", Jan. 2007, p. 4.

Holmes, "Leukocyte Analysis and Differentiation Using High Speed Microfluidic Single Cell Impedance Cytometry", "Lab on a Chip", 2009, pp. 2881-2889, vol. 9, No. 20, Publisher: The Royal Society of Chemistry.

Huang, Y., et al., "MEMS-Based Sample Preparation for Molecular Diagnostics", "Ananlytical and Bioanalytical Chemistry", 2002, pp. 49-65, vol. 372, Publisher: Springer-Verlag.

Iqbal, S.S., et al., "A Review of Molecular Recognition Technologies for Detection of Biological Threat Agents", "Biosensors and Bioelectronics", 2000, pp. 549-578, vol. 15, Publisher: Elsevier Science S.A.

Ishii, J.K., et al., "Bead-Based Sandwich Hybridization Characteristics of Oligonucleotide-Alkaline Phosphatase Conjugates and Their Potential for Quantitating Target RNA Sequences", "Bioconjugate", 1993, pp. 34-41, vol. 4, Publisher: American Chemical Society.

Iwadate, Y., et al., "Molecular Dynamics and Forces of a Motile Cell Simultaneously Visualized by TIRF and Force Microscopies", "BioTechniques", May 2008, pp. 739-750, vol. 44, No. 6, Publisher: MDS Analytical Technologies.

Jacobsen, N., et al., "Direct Isolation of Poly(A)+ RNA from 4 M Guanidine Thiocyanate-Lysed Cell Extracts Using Locked Nucleic Acid-Oligo(T) Capture", "Nucleic Acids Research", 2004, p. e64, vol. 32, No. 7, Publisher: Oxford University Press.

Jarvius, Jonas, "DNA Tools and Microfluidic Systems for Molecular Analysis", "Digital Comprehensive Summaries of Uppsala Dissertations from the Faculty of Medicine", 2006, pp. 66, vol. 161, Publisher: Acta Universitatis Upsaliensis.

Jokerst, J.V., et al., "Integration of Semiconductor Quantum Dots into Nano-Bio-Chip Systems for Enumeration of CD4+ T Cell Counts at the Point-of-Need", "Lab on a Chip", 2008, pp. 2079-2090, vol. 8, Publisher: The Royal Society of Chemistry.

Rosen, Shara, "The Worldwide Market for In Vitro Diagnostic Tests", "6th Edition", Jun. 2008, pp. 938, Publisher: Kalorama Information.

Kell, A.J., et al., "Superparamagnetic Nanoparticle-Polystyrene Bead Conjugates as Pathogen Capture Mimics: A Parametric Study of Factors Affecting Capture Efficiency and Specificity", "Langmuir", 2008, pp. 3493-3502, No. 24, No. 7, Publisher: ACS Publications.

Kim, K., et al., "Thin-Film-Based Sensitivity Enhancement for Total Internal Reflection Fluorescence Live-Cell Imaging", "Optics Letters", Nov. 1, 2007, pp. 3062-3064, vol. 32, No. 21, Publisher: Optical Society of America.

Kleines, M. et al., "Efficient Extraction of Viral DNA and Viral RNA by the Chemagic Viral DNA/RNA Kit Allows Sensitive Detection of Cytomegalovirus, Hepatitis B Virus, and Hepatitis G Virus by PCR", "Journal of Clinical Microbiology", Nov. 2003, pp. 5273-5276, vol. 41, No. 11, Publisher: American Society for Microbiology.

Kusnezow, W., et al., "Optimal Design of Microarray Immunoassays to Compensate for Kinetic Limitations", "Molecular & Cellular Proteomics 5.9", 2006, pp. 1681-1696, Publisher: The American Society for Biochemistry and Molecular Biology, Inc.

Kwakye, S., et al., "A Microfluidic Biosensor Based on Nucleic Acid Sequence Recognition", "Analytical and Bioanalytical Chemistry", 2003, pp. 1062-1068, vol. 376, Publisher: Springer-Verlag.

Layne, S.P., et al., "High Speed, High Volume Laboratory Network for Infectious Diseases and Center for Rapid Influenza Surveillance and Research", Sep. 22, 2008, pp. 17 Publisher: University of California Los Angeles.

Wellman A.D. et al. "Multiplexed, Waveguide Approach to Magnetically Assisted Transport Evanescent Field Fluoroassays", Anal. Chem Sep. 1, 2007 vol. 79, No. 1, 6622-6628.

Choi J-W et al. "A new magnetic bead-based, filterless bio-separator with planar electromagnet surfaces for integrated bio-detection systems", Sensors and Actuators B 68 (2000) 34-39.

Su, X-L et al. "Quantum dot biolabeling coupled with immunomagnetic separation for detection of *Escherichia coli* O157:H7" Anal. Chem. 2004 76, 4806-4810.

Zhao, Y. et al. "Simultaneous Detection of Multifood-Borne Pathogenic Bacteria Based on Functionalized Quantum Dots Coupled with Immunomagnetic Separation in Food Samples", J. Agric. Food Chem. 2009 57, 517-524.

Myatt, C. J.. et al. Low-cost, multiplexed biosensor for disease diagnosis, Proc. of SPIE, 2009, vol. 7167, 716703-09.

European Application No. 10812709.3 Supplementary European Search Report, Apr. 9, 2013, 9 pages.

\* cited by examiner

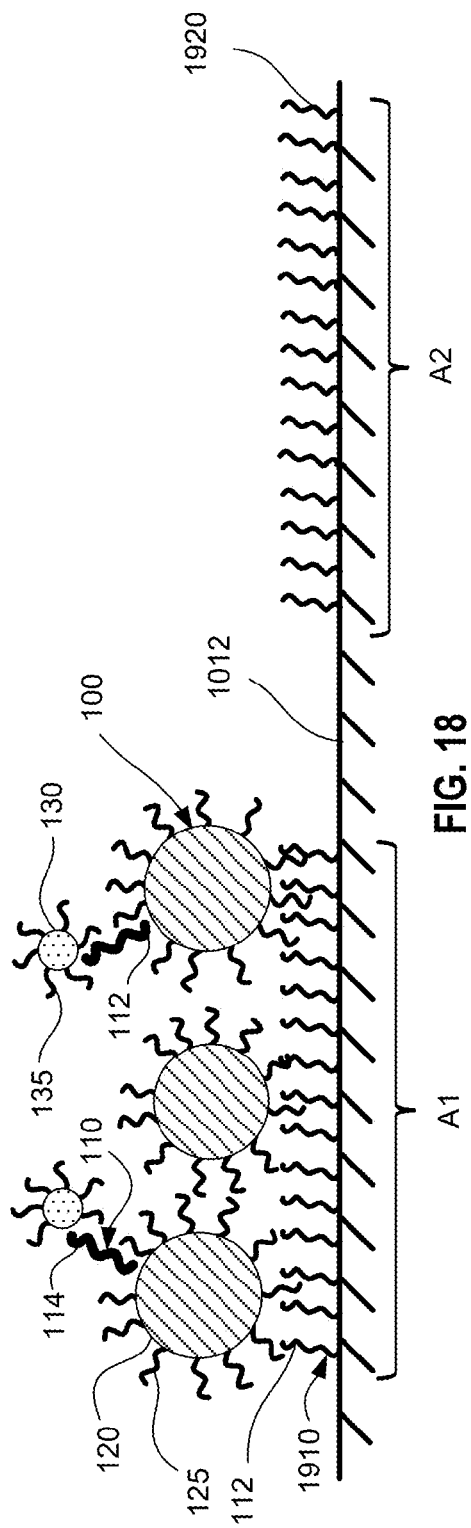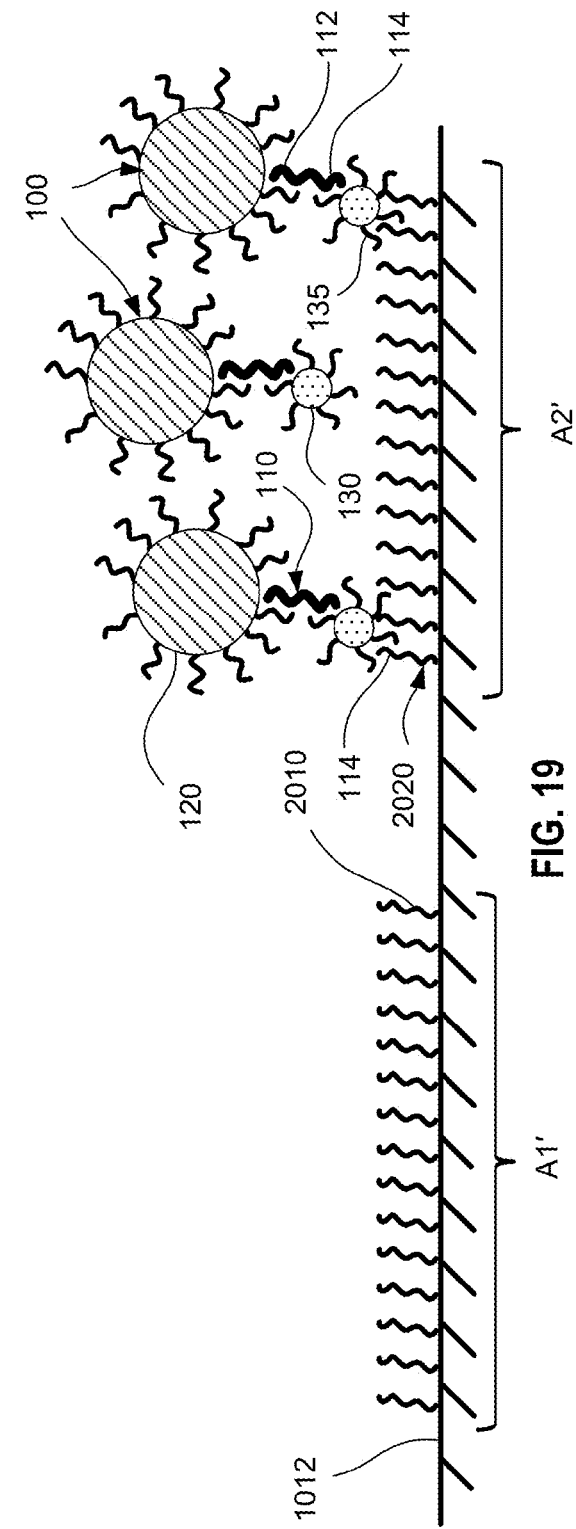

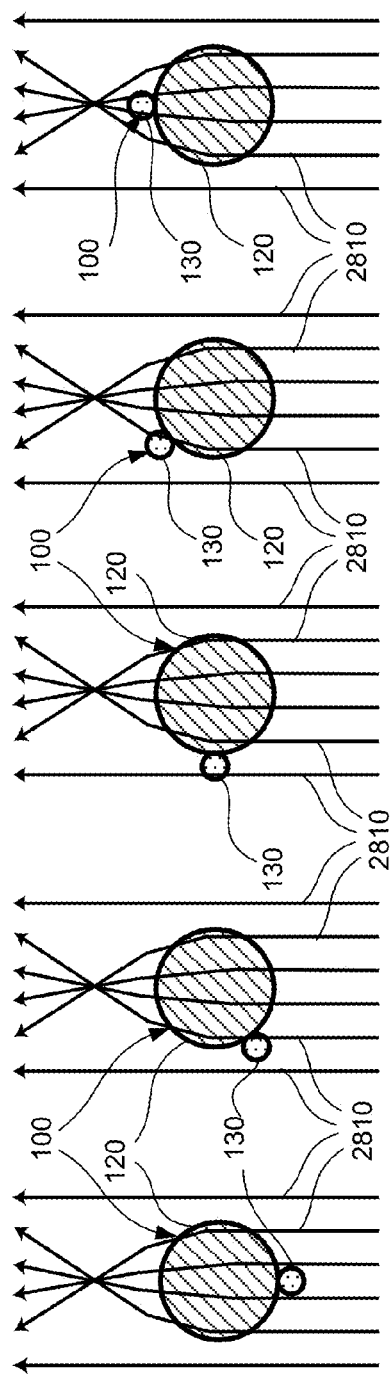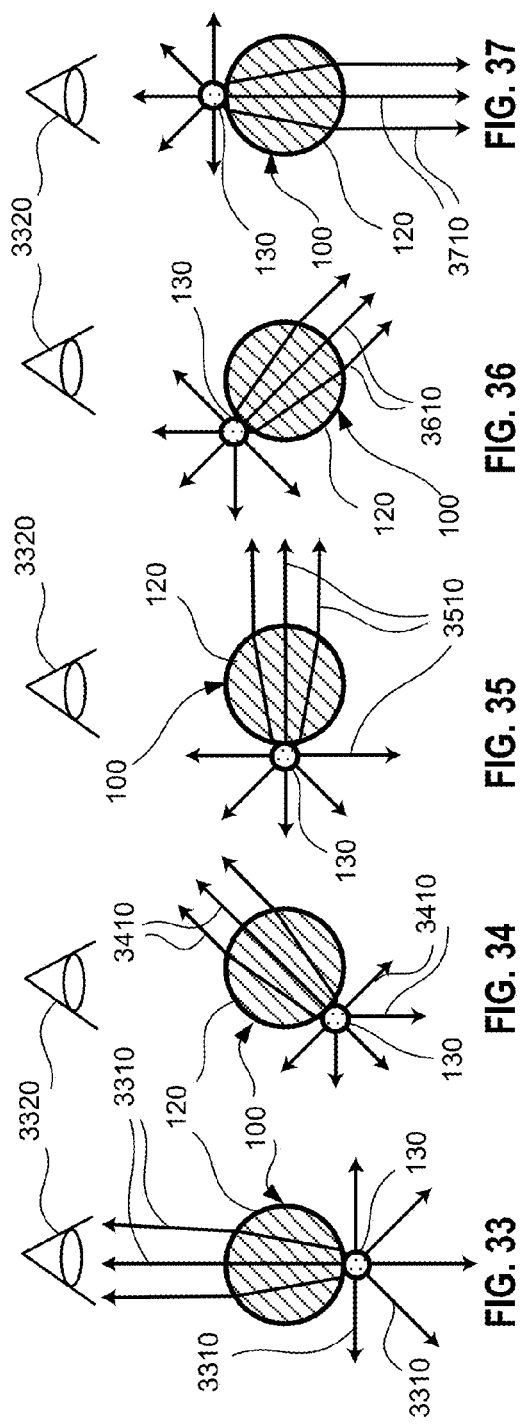

INTEGRATED SAMPLE PREPARATION AND ANALYTE DETECTION

PRIORITY AND RELATED APPLICATIONS

This application claims the benefit of Provisional U.S. Patent Application No. 61/238,376 filed on Aug. 31, 2009. The details of this Application No. 61/238,376 are incorporated by reference into the present application in its entirety and for all purposes.

GOVERNMENT INTEREST

This invention was made with government support under contract AI065357 awarded by the U.S. National Institute of Health. The Government has certain rights in this invention.

BACKGROUND

Methods for measuring target analytes in biological samples, including bodily fluids (e.g., blood, urine, nasal washes), environmental samples, and bioprocessing samples, often require a combination of biological sample preparation followed by some specific detection assay. Analytes, such as proteins, nucleic acids and cells in biological samples, are typically a dilute component in a complex fluid or solid milieu.

Nucleic acids, such as ribonucleic acid ("RNA") and deoxyribonucleic acid ("DNA"), are particularly useful target analytes in biological assays. For example, for influenza virus detection, the target analyte may consist of RNA contained within dilute viral particles in a nasal swab. In order to prepare the biological sample, for instance, the specimen must be released from the swab, nasal mucoid matrix must be broken down and viral particles must be opened while target RNA are protected from degrading enzymes. Similar processing steps are required for nucleic acid target analytes in other biological matrices, including bodily fluids or tissues, environmental samples, forensic samples, etc. After performing the appropriate sample preparation, many advanced nucleic acid detection methods require amplification of the target analytes through methods such as polymerase chain reaction ("PCR"), nucleic acid sequence-based amplification ("NASBA"), transcription-mediated amplification ("TMA"), loop-mediated isothermal amplification ("LAMP") or other enzymatic amplification techniques. All of these methods have varying degrees of sensitivity to contaminants in the target matrix, therefore careful sample preparation is required. Finally, amplification is typically coupled with some type of signal transduction in order to measure the amplified product.

Other useful target analytes include peptides, antigens, antibodies, and other proteins. Often these targets are extremely dilute (e.g., antigen concentrations of picograms per milliliter of blood) in a complex matrix containing debris, a variety of cell types, and a large background of proteins that can be in concentrations many orders of magnitude higher than the target analyte. Common approaches to the detection of peptide or protein targets are variations of the sandwich immunoassay, which uses antibodies with specific affinity to the target analyte to selectively immobilize and detect the target. Signal transduction in immunoassays is often based on antibodies labeled with some signal transduction means, such as enzymes used to drive color changes in the enzyme-linked immunosorbent assay ("ELISA"), fluorescent labels used in the fluorescence immunoassay ("FIA"), chemiluminescence and radioactive labels. Particle agglutination assays and immunochromatographic assays are examples of immunoassays based on particle assembly to yield a visible signal. In histology, fluorescence microscopy and flow cytometry applications, analysis of cell populations also typically requires an immunostaining step, where labeled analyte-specific antibodies are used to colorimetrically or fluorescently label the target analytes. Magnetic particles can also be used as labels for magnetic signal transduction.

Whole cells (e.g., mammalian, plant, or bacteria) and viral particles define another class of target analyte. Again, target analyte cells or particles are frequently found at low concentration in complex sample milieu. For example, clinically relevant bacterial concentrations in blood are 1 to 10 colony forming units per milliliter. Extensive and complex sample preparation and labeling are typically required for detection of cellular targets.

Functionalized particles, including microspheres, beads and nanoparticles, have been used for numerous biological assay applications. Several approaches are highlighted below.

Particle-Based Sample Preparation: Functionalized magnetic particles and beads have been used in the context of biological sample cleanup, concentration and separation. Magnetic particles are commercially available in a range of sizes, carrier matrices (e.g., polymer, silica), designs (e.g., core-shell, embedded iron oxide nanoparticles) and surface chemistries. Magnetic particles enable sample manipulation without expensive or complex equipment requirements. Non-magnetic particles are also used in biological sample preparation. One example is the use of silica particles in the presence of chaotropic buffers to selectively bind nucleic acids.

Particle-Based Detection: Particles can be used to provide detection or signal transduction in biological assays. Exemplary methods include latex agglutination assays, immunochromatographic assays, light scattering assays, and fluorescent particle assays. Agglutination assays are simple, visually-read assays, in which the presence of a target analyte causes agglutination or flocculation of functionalized latex particles. Lateral flow assays and other immunochromatographic methods are also typically visually-read assays, in which particles with specific binding groups (e.g., antibodies) migrate through porous material and, in the presence of the target analyte, accumulate on a line or spot in the porous material where specific binding groups have been immobilized. Numerous particle types (e.g., colored latex, gold, and selenium colloids) are used in immunochromatographic assays. The main disadvantages of the latex agglutination and immunochromatographic approaches are limited sensitivity and limited multiplexing ability. The visual read also renders these techniques qualitative and subjective.

Another particle-based approach to target analyte detection is the use of fluorescently-labeled particles to provide signal transduction in biological assays. Polymer and glass particles containing fluorescent dyes and other luminophores such as lanthanide chelates are commercially available (e.g., Molecular Probes/Invitrogen, Thermo Scientific) and are supplied with surface reactive groups for performing further functionalization. Fluorescent particles have been used in the context of planar waveguide-based detection, and multiple analyte detection methods, based on multiplexed measurement of different fluorescently labeled particles, have been demonstrated (see U.S. patent application Ser. No. 12/617,535, by Moll et al., entitled WAVEGUIDE WITH INTEGRATED LENS and filed 12 Nov. 2009, which is incorporated herein by reference in its entirety). Light scattering particles have also been employed for analyte detection, including light scattering particles bound at planar waveguide surfaces.

Field-Assisted Particulate Assays: Mass transport represents a serious limitation in practical heterogeneous assays performed at solid surfaces. This limitation is particularly important in low volume liquid systems where convective mixing is limited. Suggested methods to overcome mass transport limitations include electrophoretic approaches for concentration and detection of nucleic acids, proteins, and whole cells, and methods that use magnetic particle labels.

Dual-Particle Approaches: Several dual-particle approaches have been described, such as an approach in which latex particle pairs are formed in the presence of a target analyte, enabling proximity-based signal generation via a donor-acceptor oxygen channeling mechanism. Additionally, a system for detection of nucleic acid sequences has been described, which utilizes a magnetic particle with a target-specific oligonucleotide sequence and a dye-encapsulated liposome also with a target-specific oligonucleotide sequence. The particle-liposome combination is used as a sensor for specific RNA targets. In a set of approaches collectively referred to as 'biobarcode' assays, a large number of copies of a barcode sequence molecule are generated in the presence of an analyte. Alternatively, self-calibrating assays utilize particle complexes and dual wavelength detection.

A variety of useful particle-based separation and purification methods are available for processing biological samples for subsequent detection assays. The particle-based systems provide a method of signal transduction, and can serve as a detection mode in different biological assay formats. Most of these approaches, however, typically require multiple sample preparation and analyte detection steps with extensive user or machine interventions.

SUMMARY

In an embodiment, a system for sample preparation and analyte detection is disclosed. The system includes a cartridge, which cartridge includes a fluidic channel, a waveguide, and a capture spot disposed on the waveguide and within the fluidic channel. The system further includes a force field generator, an imaging system, and a fluid. The fluid includes a sample, which potentially contains a target analyte. The fluid further includes first type particles, which include binding moieties specific for the target analyte and is responsive to a force field, and second type particles, which include binding moieties specific for the target analyte and is capable of generating a signal. When the sample contains the target analyte, specific binding interactions between the target analyte and binding moieties on the first and second type particles cause at least one of the first type particles and at least one of the second type particles to become linked via the target analyte to form a multiple-particle complex. Furthermore, when the fluid is brought into contact with the capture spot, the multiple-particle complex is capturable at one or more of the capture spots. Still further, the force field allows manipulation of at least one of the first type particles, second type particles and multiple-particle complex such that the signal, generated by the second type particles and captured at the imaging system, is indicative of presence of the target analyte within the sample.

In a further embodiment, the first type particles are magnetic particles, and the force field generator is a magnet. For example, the magnetic particles are polystyrene microspheres including a magnetic component.

In a still further embodiment, the multiple-particle complex exhibits directional signal enhancement.

In a yet further embodiment, the second type particles are luminescent particles.

In further embodiment, the system also includes an excitation source for providing excitation energy so as to illuminate at least a portion of the fluidic channel. The second type particles are fluorescent particles configured for generating a fluorescent signal when the excitation energy is incident thereon.

In a yet further embodiment, the waveguide is a planar waveguide such that the excitation energy is directed into the portion of the fluidic channel at least in part by total internal reflection through the planar waveguide.

In a still further embodiment, the cartridge includes a plurality of capture spots disposed on the waveguide and within the fluidic channel.

In a further embodiment, the imaging system includes an image sensor selected from a group consisting of a charge-coupled device ("CCD") and a complementary metal-oxide-semiconductor ("CMOS") sensor.

In another embodiment, a method for sample processing and target detection is disclosed. The method includes providing a sample, which sample potentially contains a target analyte. The method also includes providing particles of a first type, which includes binding moieties specific for the target analyte and being responsive to a force field. The method further includes providing particles of a second type, which also includes binding moieties specific for the target analyte and being capable of generating a signal. The method further includes contacting the sample with the first and second type particles under conditions that allow specific binding interactions between the target analyte and binding moieties on the first and second type particles such that, in the presence of the target analyte, one of the first type particles and one of the second type particles are linked via the target analyte to form a multiple-particle complex. The method further includes manipulating at least one of the first and second type particles and the multiple-particle complex using the force field. Finally, the method includes detecting the multiple-particle complex in a manner that is sensitive to the multiple-particle complex and not to individual ones of the first and second type particles, wherein the multiple-particle complex so detected is indicative of the target analyte.

In a further embodiment, manipulating at least one of the first and second type particles and the multiple-particle complex comprises applying a magnetic field to at least a portion of the first and second type particles and the multiple-particle complex. In a still further embodiment, manipulating includes separating the first type particles and the multiple-particle complex from the second type particles.

In a yet further embodiment, the second type particles may include luminescent molecules or ions. In a still further embodiment, the second type particles generate the signal upon exposure to excitation energy. Furthermore, in another embodiment, illuminating includes containing and guiding the excitation energy within a volume such that only the first type particles, second type particles and multiple-particle complex disposed adjacent to the volume is illuminated. Still further, manipulating includes moving the second type particles away from the volume such that only the first type particles and multiple-particle complex are illuminated.

In a still further embodiment, manipulating includes exposing the sample to the force field so as to retain the multiple-particle complexes while removing from the sample the second type particles that are unlinked to the target analyte. The method further includes providing an excitation energy to the sample such that the second type particles, linked in the multiple-particle complexes so retained in the sample, generate a detectable signal.

In a further embodiment, the multiple-particle complex exhibits directional signal enhancement, and detecting the multiple-particle complex includes sensing the detectable signal in a manner sensitive to the directional signal enhancement.

BRIEF DESCRIPTION OF THE FIGURES

FIGS. 18 and 19 provide exemplary schematics showing possible surface hybridization modes for the particle complexes.

FIGS. 28-37 provide exemplary schematics showing the directionality of fluorescence signal enhancement and light collection effects provided by the combination of the particles within the multiple-particle complex.

Figure 1:
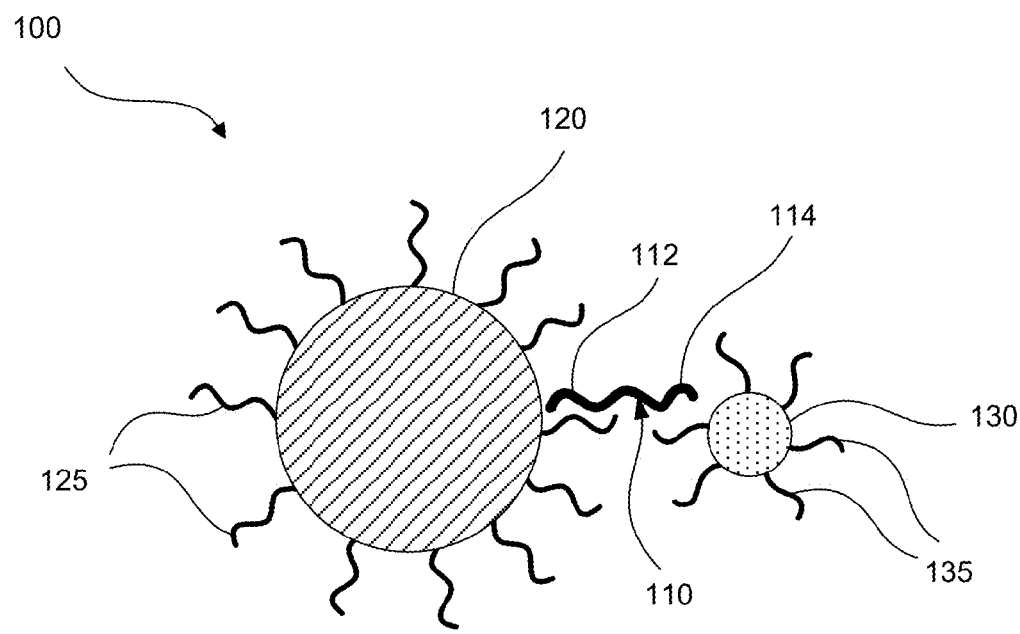
FIGS. 1 and 2 show exemplary schematics of multiple-particle complex formation for nucleic acid, protein and cellular targets.

It is noted that, for purposes of illustrative clarity, certain elements in the drawings may not be drawn to scale.

DETAILED DESCRIPTION

The embodiments described herein address the need for simplified, integrated sample preparation and detection systems for biological assays. Exemplary embodiments address major limitations in the current art, in which sample preparation and analyte detection are performed separately, each with multiple, time-consuming or automation-intensive methods. Few, if any, previously-described approaches have successfully combined sample preparation and detection in a single, integrated method. The approach described herein addresses the significant need for simplified, integrated sample preparation and detection systems for biological assays.

Examples of analytes include nucleic acids, proteins, and cells in complex milieu, such as biological samples. For instance, the target analyte may be a protein or peptide target, and particles may be functionalized with specific binding groups such as antibodies, Fab fragments, or aptamers. A complex of at least two dissimilar particle types may be used for the integrated purification, concentration, and detection of target analytes. The multiple-particle complex may be formed, for example, when a target analyte forms the link between a field-responsive particle, such as a magnetic particle, and a signal generating particle, such a fluorescent particle. That is, the multiple-particle complex effectively acts as a sandwich assay.

The terms "particles" and "beads" are used interchangeably herein, and may refer to any of several particles of different compositions ranging in size from approximately 0.01 to 20 micrometers in diameter. Particles may include organic materials such as, but not limited to, latex, polystyrene, agarose and lipids. While particles are spherical (e.g., latex microspheres) in many cases, the particles disclosed herein are not required to be spherical. Particles may also include inorganic materials such as, but not limited to, silica and other silica-based glass compositions, oxides including iron oxides, ceramics and semiconductors. Particles may also be composite constructions, such as core-shell particles (e.g., a metal or metal oxide core with an organic polymer shell), and polymers incorporating metal oxide subparticles therein.

FIG. 1 shows an illustration of the formation of a multiple-particle complex by the linking of a particle of a first type and another particle of a second type via a target analyte, in accordance with an embodiment. A complex 100 includes a target analyte 110, which is shown here as a nucleic acid strand. Target analyte 110 includes a first end sequence 112 and a second end sequence 114. A first type particle 120 has been functionalized with a first probe 125 (e.g., a "capture probe"), complementary to first end sequence 112 of target analyte 110. First type particle 120 may be, for example, a field-responsive particle, such as a magnetic particle, that has been functionalized with a capture sequence complementary to first end sequence 112 of target analyte 110. As a particular example, first probe 125 may be a 50 nucleotide, single-stranded DNA capture sequence. A field-responsive particle may be any particle that responds to an external force field such as, but not limited to, a magnetic field, an electric field and gravitational or sedimentation field.

Continuing to refer to FIG. 1, a second type particle 130 has been functionalized with a second probe ("detect probe") 135, which is complementary to second end sequence 114 of target analyte 110. For example, second type particle 130 may be a signal particle, such as a fluorescent particle, that has been functionalized with a DNA sequence complementary to second end sequence 114. A signal particle (or a signal generating particle) may be any particle that generates a detectable signal, such as a luminescent particle that emits light when excited with an appropriate illumination source. Examples of detectable signals include, but are not limited to, luminescence, fluorescence, phosphorescence, chemiluminescence, light scattering and magnetic fields. Complex 100 exhibits a combination of the characteristics of first and second type particles 120 and 130, respectively. For example, if first type particle 120 is a magnetic particle, and second type particle 130 is a fluorescent particle, then complex 100 may be manipulated by application of a magnetic field, and also be induced to generate a fluorescent signal by application of appropriate excitation energy, such as light from a laser or a light-emitting diode ("LED").

In various embodiments, target analyte 110 forms a bridge between at least two dissimilar particles, each with distinct functionality. One particle type (e.g., first type particle 120) may be responsive to a force field (i.e., a field-responsive particle), allowing the separation, purification and/or concentration of these particles with the application of an appropriate force field. For example, the field-responsive particle may be a paramagnetic particle, which is responsive to a magnetic field from a permanent magnet or electromagnet. The field-responsive particle may also include other magnetic particle types. Additional types of particles suitable for use as field-responsive particles may be sedimenting particles, such as particles with sufficient density relative to the fluid density to allow sedimentation, either in a natural gravitational field or through centrifugation, and particles with electrophoretic mobility (i.e., particles responsive to an applied electric field).

Furthermore, second type particle 130 may be, for example, a latex or glass particle impregnated with fluorescent molecules, luminescent particles (e.g., particles impregnated with lanthanide chelates), light scattering particles, resonant light scattering particles, nanoparticles, and/or magnetic particles. Both first and second type particles 120 and 130 may require functionalization with binding moieties that make them amenable to biological assays. Particle functionalization protocols are established in the art, and kits for magnetic particle and fluorescent particle functionalization are commercially available.

Figure 2:
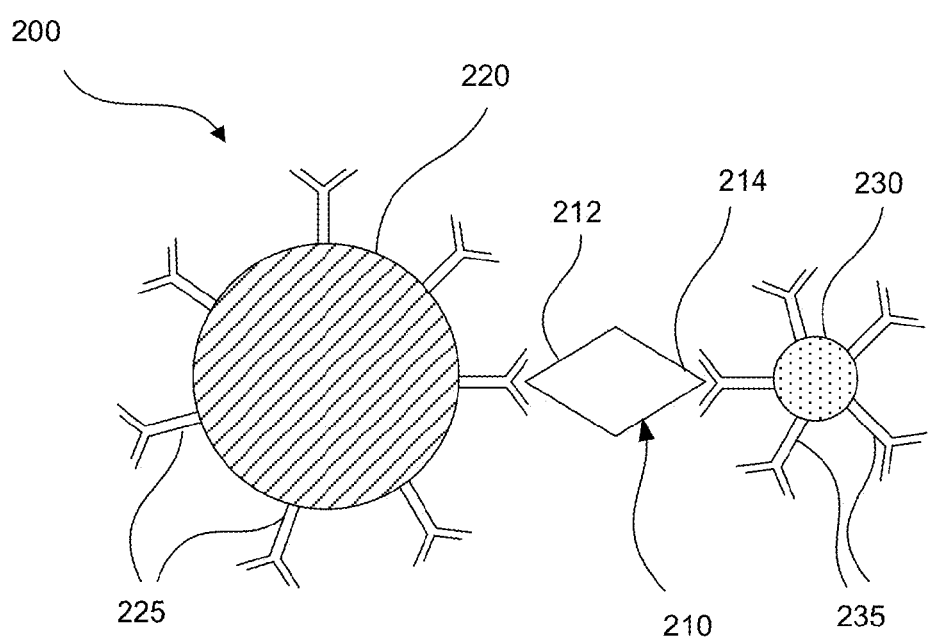

FIG. 2 shows an illustration of another approach to formation of a multiple-particle complex, in accordance with an embodiment. In this case, a first type particle and a second type particle are linked via a target analyte, where the target analyte is an antigen such as, for example, a protein, bacteria, or cell. A complex 200 includes a target analyte 210. Target analyte 210 includes a first epitope region 212 and a second epitope region 214. A first type particle 220 has been functionalized with a first specific-binding ligand 225, such as an antibody, which has been selected for having a specific affinity to first epitope region 212 of target analyte 210. First type particle 220, again, may be a field-responsive particle, such as a magnetic particle. A second type particle 230 has similarly been functionalized with a second specific-binding ligand 235, which has been selected for having a specific affinity to second epitope region 214 of target analyte 210. Second type particle 230 may be, for example, a signal particle, such as a fluorescent particle that generates a fluorescent signal by application of appropriate excitation energy.

In one embodiment, nucleic acid target is rapidly concentrated and detected using magnetic particles functionalized with oligonucleotide capture probes complementary to the target nucleic acid sequence and fluorescent particles functionalized with oligonucleotide probes complementary to a different section of the target sequence. Simple wash steps may be performed using magnetic washes, and a magnet is then used to drive particle pairs to a detection surface where particle complexes are quantified. FIGS. 3-6 are a series of drawings illustrating an exemplary process for such sample preparation and multiple-particle complex formation and detection.

Figure 3:
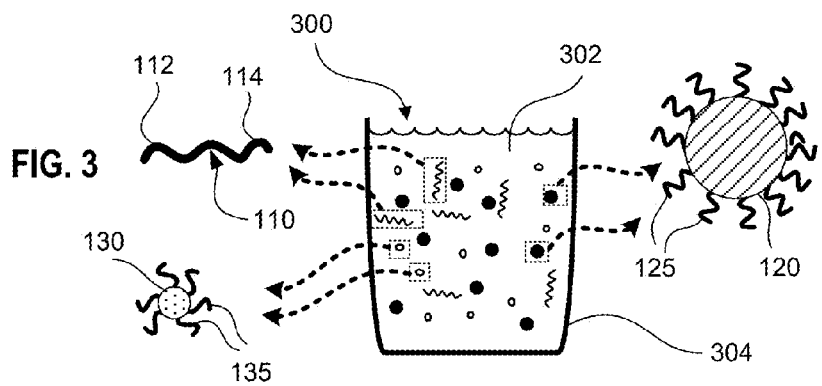
FIGS. 3-6 provide an exemplary schematic of sample clean-up, multiple-particle complex formation and analyte detection, in accordance with an embodiment.

First referring to FIG. 3 in conjunction with FIG. 1, a buffer 302 is confined within a container 304. A sample, such as blood, serum, or other biological specimen containing a target analyte 110, is added to buffer 302. Buffer 302 may be, for example, a lysis buffer or a stabilization buffer containing functionalized particles. In the exemplary process shown in FIG. 3, buffer 302 contains first and second type particles 120 and 130, respectively, which have been functionalized, as previously discussed. For example, as shown in FIGS. 1 and 3, first type particle may be a magnetic particle, which functionalized with capture probes 125 suitable for binding to first end sequence 112 of the specific target analyte of interest. Also, second type particles 130 may be a fluorescent particle, which has been functionalized with detect probes 135 suitable for binding to second end sequence 114 of target analyte 110.

Figure 4:
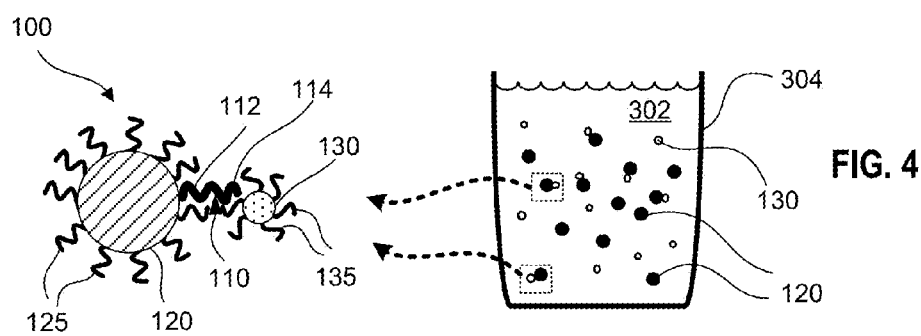
Figure 5:
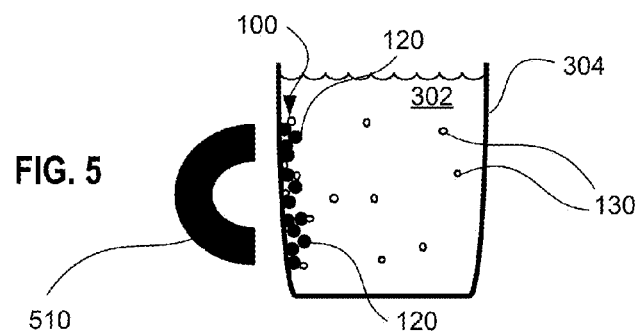

Referring to FIG. 4, hybridization leads to the formation of multiple-particle complexes 100. Each one of multiple-particle complexes 100 is formed by capture probe 125 of first type particle 120 binding to first end sequence 112 of target analyte 110, and detect probe 135 of second type particle 130 binding to second end sequence 114 of target analyte 110. Unbound first and second type particles 120 and 130, respectively, remaining in buffer 302 then are removed by one or more "wash" steps, as shown in FIG. 5. Taking advantage of the magnetic nature of first type particles 120, a magnet 510 is brought into proximity of container 304 such that multiple-particle complexes 100 as well as unbound first type particles 120 are pulled toward magnet 510, while unbound second type particles 130, which are non-magnetic, remain suspended in buffer 302. By a series of fluid exchange (i.e., "wash") steps, substantially all of unbound second type particles 130 may be removed from container 304. It may be noted that unbound, first type particles 120 need not be removed by wash steps because they do not generate a signal that is detectable in the detection step, which is illustrated in FIG. 6.

Figure 6:
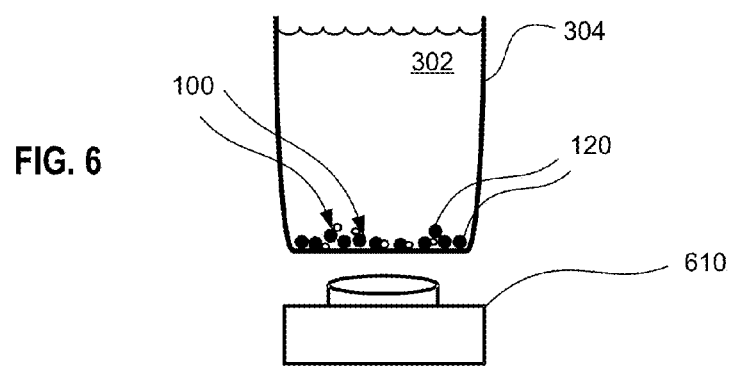

Following the wash steps, magnet 510 is removed and the remaining multiple-particle complexes 100 and unbound first type particles 120 are allowed to settle at the bottom of container 304, as shown in FIG. 6. Alternatively, multiple-particle complexes 100 and unbound first type particles 120 may be magnetically concentrated at the bottom of container 304. Second type particles 130, bound to target analyte 110 within multiple-particle complexes 100, are excited with an appropriate excitation energy (not shown), and the resulting signal from second type particles is detected by an imaging system 610.

Figure 7:
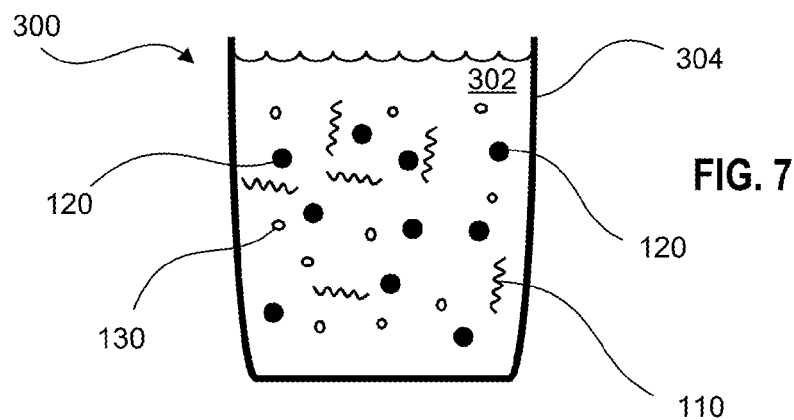
FIGS. 7-9 provide an exemplary schematic of multiple-particle complex formation and detection without a separate wash step, in accordance with an embodiment.
Figure 8:
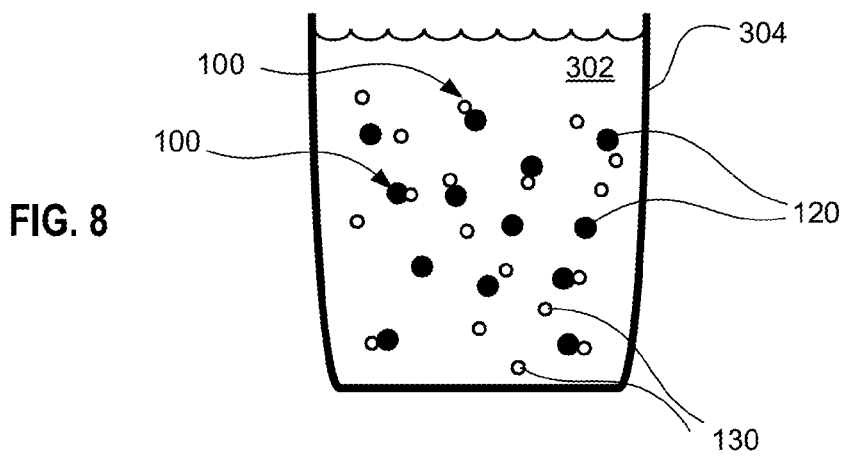
Figure 9:
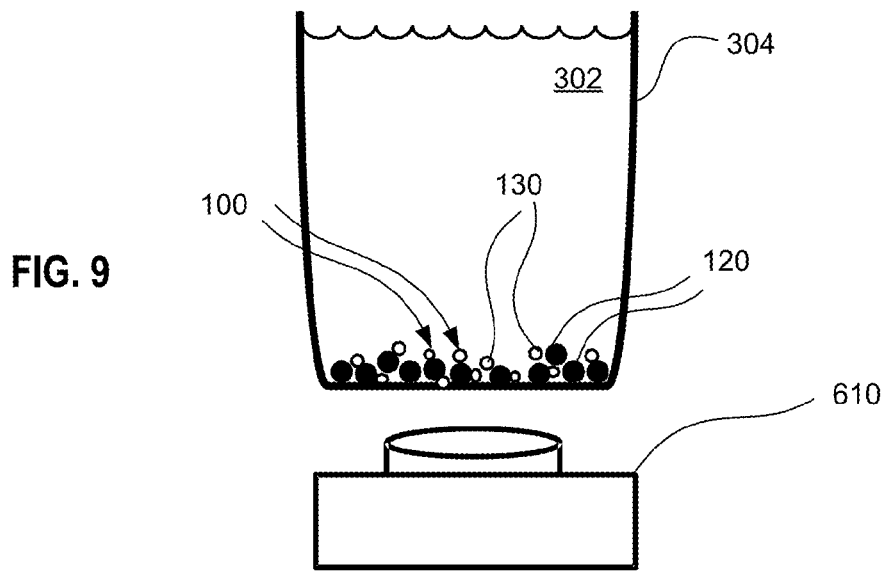

An alternative method of sample preparation and analyte detection without a "wash" step is shown in FIGS. 7-9. In this embodiment, all particles, including multiple-particle complexes as well as unbound first type and second type particles are present at the bottom of container 304, and a detection method that is sensitive only to multiple-particle complexes is used for target analyte detection. As shown in FIG. 7, which is similar to FIG. 3, buffer 302 within a container 304 contains a plurality of target analyte 110, first type particle 120 and second type particle 130. As shown in FIG. 8 (which is similar to FIG. 4), target analyte 110 links together first and second type particles 120 and 130, respectively, so as to form a plurality of multiple-particle complexes 100. In contrast to the method described in relation to FIGS. 3-6, this alternative method eliminates the wash step shown in FIG. 5. Then, as shown in FIG. 9, a detection method sensitive only to the presence of multiple-particle complexes 100 is used to detect the presence of the target analyte. An example of such a detection method is described in Example VII below.

The processes shown in FIGS. 3-9 may be adapted to affect spatial translation of the target analyte and/or multiple-particle complexes by using the processes in combination with a fluidic channel and a magnetic arrangement, such as a movable set of magnets or a plurality of magnets that may be activated and deactivated at will (e.g., electromagnets). An example of such a spatial translation process, suitable for integrated sample preparation and analyte detection, is illustrated in FIGS. 10-17.

Figure 10:
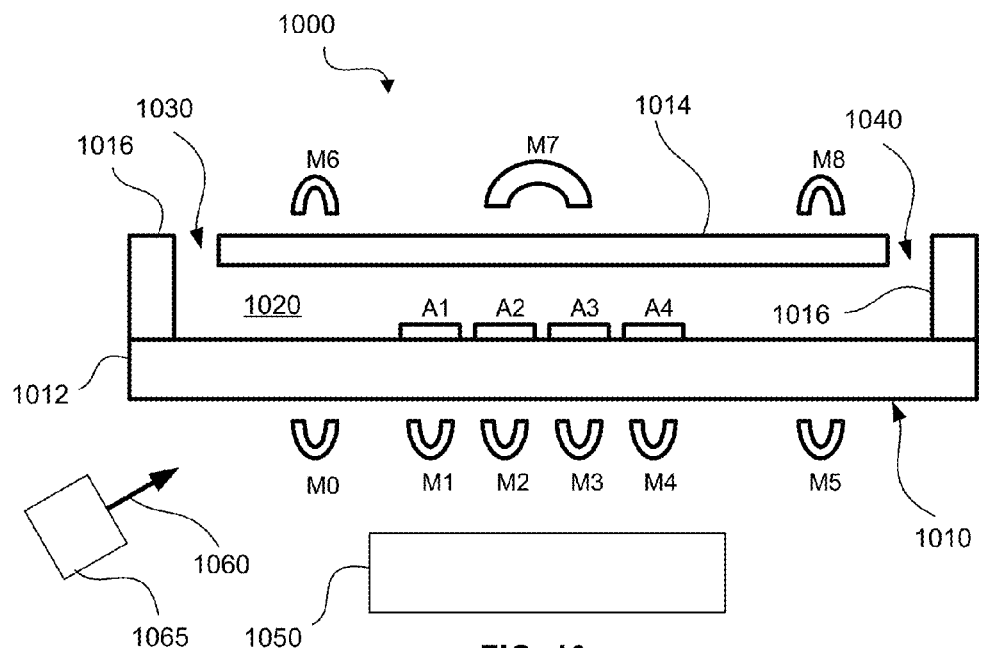
FIGS. 10-17 provide an exemplary schematic of a method for using a fluidic cartridge and an apparatus that uses magnetic fields to move particle complexes across a surface including an array of capture spots.

FIG. 10 shows a system 100 including a cartridge 1010, which is formed from a substrate 1012, an upper component 1014, and a gasket 1016 defining a fluidic channel 1020. Alternatively, substrate 1012 and/or upper component 1014 may include integrally-formed side walls (not shown), in place of gasket 1016, such that the combination of substrate 1012 and upper component 1014 alone defines fluidic channel 1020. Fluidic channel 1020 includes an inlet port 1030 and an outlet port 1040 such that a fluid may be introduced through inlet port 1030 then removed through outlet port 1040. An array of capture spots (shown as A1-A4 in FIG. 10) is printed on substrate 1012. Capture spots may include immobilized biomolecules such as antigens, antibodies, proteins, peptides, glycans, or nucleic acids. various methods of preparing printed arrays, including contact printing, inkjet printing, piezoelectric printing, and solenoid valve jet printing are available. M0-M8 show different positions for the placement of a magnet for use in the spatial translation process. Fixed magnets may be translated to different positions during the assay, or electromagnets may be configured to be turned on and off in order to create translating magnetic fields at these positions. An imaging system 1050 may be used to capture images of optical signals generated at capture spots A1-A4 by excitation 1060 from a light source 1065.

Figure 11:
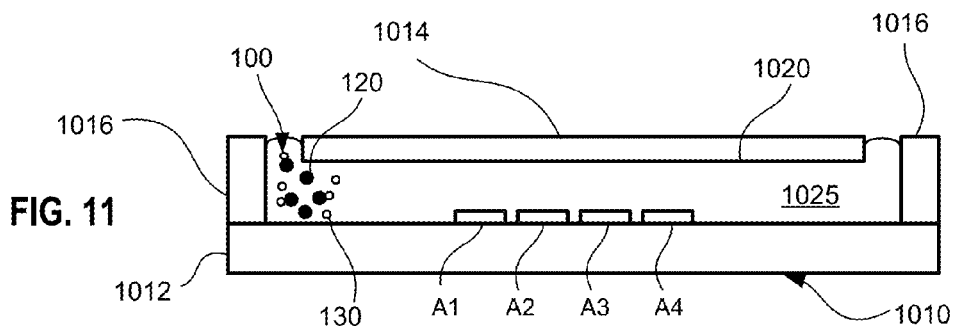

In one embodiment, referring to FIG. 11, channel 1020 is pre-filled with a buffer 1025. A sample is then introduced at inlet port 1030. The sample contains a combination of target analyte 110, first and second type particles 120 and 130, and multiple-particle complexes 100 formed by a combination of target analyte 110 linking first and second type particles 120 and 130 therewith.

Figure 12:
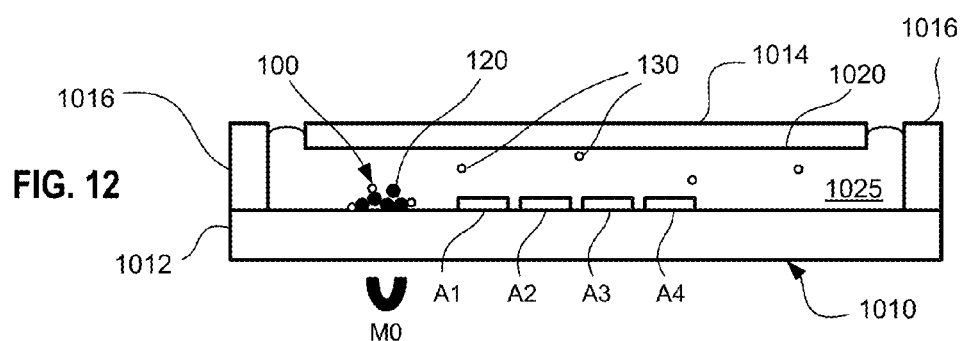

Referring now to FIG. 12, a fixed magnet or electromagnet at position M0 is activated, then an additional amount of buffer 1025 is added at inlet port 1030. The additional buffer causes flow through fluidic channel 1020, such that unbound second type particles are flushed to outlet port 140 while first type particles 120 and multiple-particle complexes 100 are retained upstream from the array of capture spots.

Figure 13:
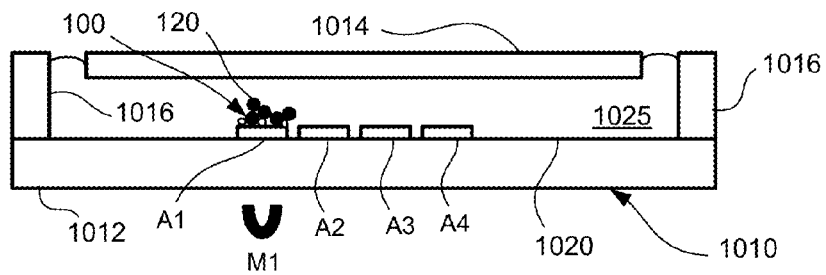

As shown in FIG. 13, a second electromagnet, located at position M1 beneath capture spot A1, is then activated such that the remaining first type particles 120 and multiple-particle complexes 100 migrate over capture spot A1. Alternatively, a fixed magnet may be moved from position M0 to position M1 beneath capture spot A1 and be activated for a certain amount of time (e.g., 5 seconds). The magnet is then deactivated to allow first type particles 120 and multiple-particle complexes 100 to freely interact with immobilized capture molecules at spot A1. Modes of capture molecule immobilization and binding to a capture spot are described in the descriptions of FIGS. 18 and 19 below. If a specific binding event occurs (e.g., antigen-antibody, protein-protein, of nucleic acid hybridization), then first type particles 120 and multiple-particle complexes 100 become bound at spot A1.

Figure 14:
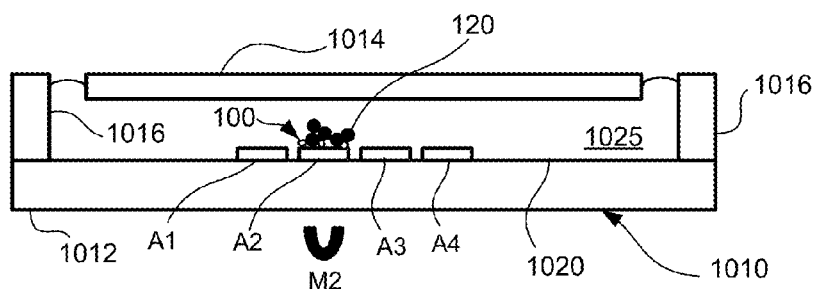
Figure 15:
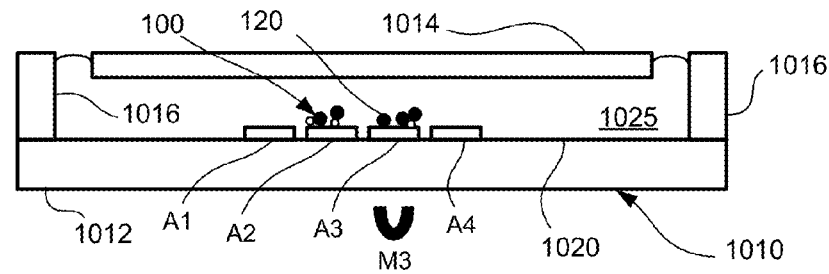
Figure 16:
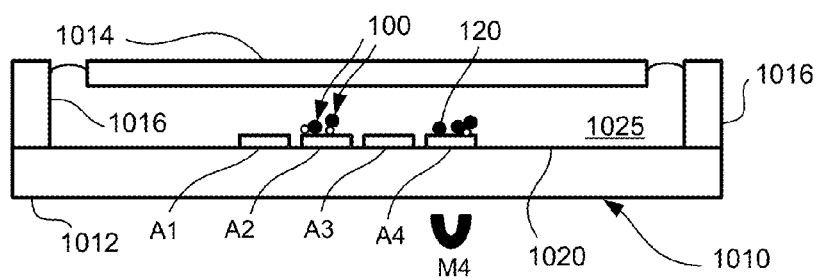

After a set amount of time (e.g., 20 seconds), an electromagnet is activated beneath capture spot A2 or, alternatively, the magnet shown in FIG. 13 may be moved from position M1 to position M2 beneath capture spot A2 then activated for a predetermined amount of time (e.g., 5 seconds), as shown in FIG. 14. Consequently, first type particles 120 and multiple-particle complexes 100 that did not bind to capture spot A1 migrate toward capture spot A2. In the example shown in FIG. 14, no specific binding to spot A1 occurred, and all first type particles 120 and multiple-particle complexes 100 are magnetically transported to capture spot A2. Once the magnet at M2 is deactivated or removed, the unbound first type particles 120 and multiple-particle complexes 100 are allowed to freely interact with immobilized capture molecules at capture spot A2 for a certain amount of time (e.g., 20 seconds). The process is then repeated for the magnet positions M3 and M4 corresponding to capture spots A3 and A4, respectively, as shown in FIGS. 15 and 16, respectively. In this example, specific binding at capture spot A2 occurred, and particle complexes were retained at spot A2 during subsequent magnetic migration steps. Finally, any residual first type particles 120 and multiple-particle complexes 100 are moved away from the capture array by moving or activating the magnet to position M5.

In the method illustrated in FIGS. 10-17, the combination of the fluidic channel and the magnet configurations allows the performance of sample preparation and analyte detection within a single volume. That is, the initially-added sample, as shown in FIG. 11, may include unbound second type particles prior to introduction into channel 1020. While a sample preparation method, such as illustrated in FIGS. 3-6, may be performed separately prior to sample introduction into channel 1020, the fluidic channel and magnet configuration of FIG. 10 makes a separate sample preparation optional. Such simplification is particularly desirable in reducing the complexity of the overall assay protocol.

Figure 17:
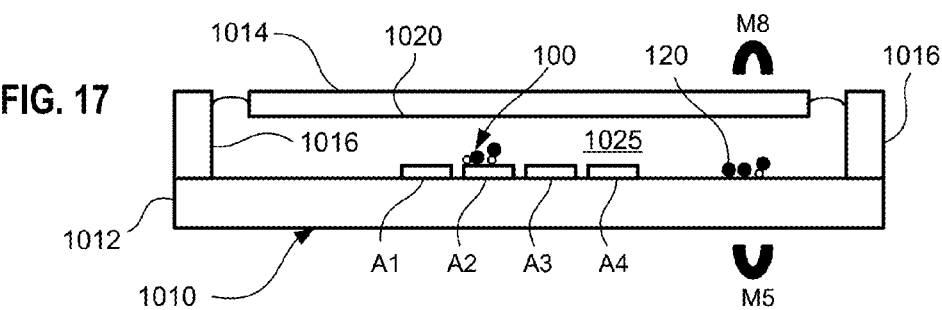

In the embodiment shown in FIGS. 10-17, magnets at positions M6 and M8 may be further configured to tune the direction of the applied magnetic field in order to alter magnetic migration velocities through the channel. For example, optionally, a fixed magnet or electromagnet at position M6 may be activated at the same time as the magnet at position M0 to assist in the flow and capture of first type particles 120 and multiple-particle complexes 100 through channel 1020, as shown in FIG. 12. Similarly, a fixed magnet or electromagnet at position M8 may also be simultaneously activated to assist in the flow of unbound first type particles 120 and multiple-particle complexes 100 toward outlet port 1040, as shown in FIG. 17.

FIGS. 18 and 19 show schematics illustrating different modes of capture molecule immobilization and binding to a capture spot. Specific binding of multiple-particle complexes 100 may be designed to occur via first probe 125 on first type particles 120 (FIG. 18) or via second probe 135 on second type particles 130 (FIG. 19). For illustration purposes, FIGS. 18 and 19 assume a nucleic acid target with oligonucleotide probes on each particle type.

Referring to FIG. 18 in conjunction with FIG. 10, capture spot A1 on substrate 1012 includes first immobilized oligonucleotide probe 1910 with first end sequence 112, complementary to the sequence of the oligonucleotide (i.e., first probe 125) immobilized on first type particle 120. Capture spot A2 includes second immobilized oligonucleotide probe 1920 with another sequence that is complementary to neither first probe 125 nor second probe 135. During an assay such as that described in FIGS. 10-17, multiple-particle complexes 100 will specifically bind to capture spot A1 through first probe 125, as will unbound first type particles 120 functionalized with first probe 125. Since capture spot A2 includes only second immobilized oligonucleotide probe 1920 with non-complementary sequences in this example, no particles of any type bind to spot A2.

Figure 20:
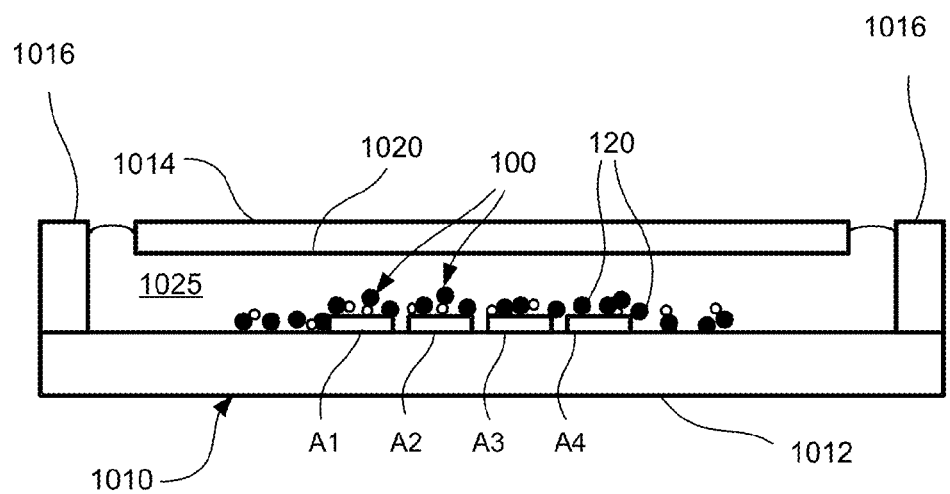
FIGS. 20-24 provide exemplary schematics showing a magnetic wash process for removing non-specifically bound particles from the imaging surface, in accordance with an embodiment.

FIG. 19 shows the alternative configuration, in which multiple-particle complexes 100 bind through second-type particle 130. In this example, capture spot A1' includes first immobilized oligonucleotide probe 2010 with a non-complementary sequence, while capture spot A2' includes second immobilized oligonucleotide probe 2020 with second end sequence 114, which is complementary to second end sequence 135 immobilized on second type particle 130. During an assay such as that described in FIGS. 10-17, multiple-particle complexes 100 and unbound second type particles 130 will specifically bind to capture spot A2' through second probe 135. No particles of any type bind to spot A1' as first immobilized oligonucleotide probe 2010 includes only a sequence that is complementary to neither first probe 125 nor second probe 135. An advantage of performing specific binding through second type particle as shown in FIG. 20, is that only multiple-particle complexes are immobilized on the capture spot, assuming unbound (i.e., free) second type particles 130 were removed from the sample prior to introduction to fluidic channel 1020. FIGS. 3-6 described a sample preparation method in which unbound second type particles may be removed from the sample for use with a capture configuration as shown in FIG. 19.

Although FIGS. 18 and 19 illustrate specific binding through oligonucleotide probes, it is recognized that the concepts shown in FIGS. 18 and 19 may readily be applied to protein or cellular targets with specific binding molecules such as peptides, proteins, antibodies, aptamers, etc.

Referring again to FIGS. 10-17, cartridge 1010, after the steps shown in FIGS. 11-17, may then be illuminated with excitation 1060 from light source 1065. Consequently, second-type particles 130, linked within multiple particle complexes 100 captured on one or more of capture spots A1-A4, generate a signal in response to excitation 1060 that may be captured by imaging system 1050 for target analyte detection.

Figure 21:
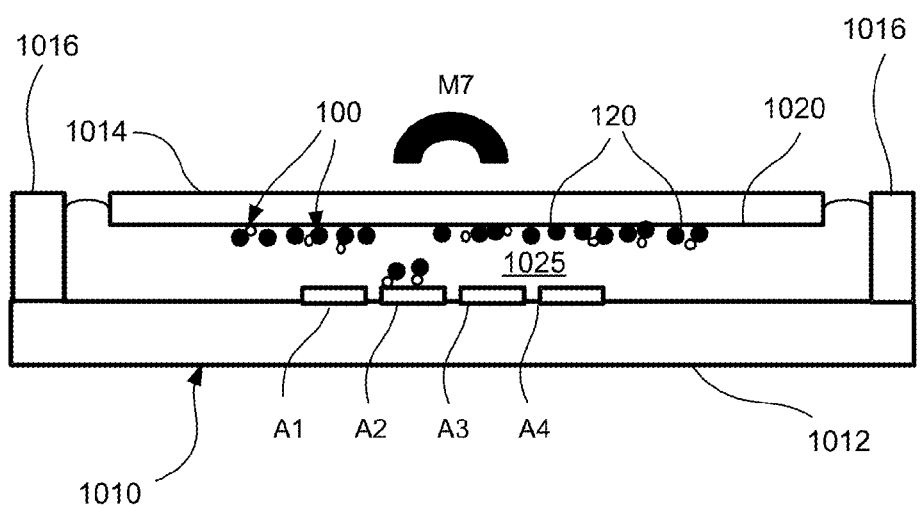

Optionally, as shown in FIGS. 20 and 21, a wash magnet 1910 may be used to provide a "magnetic wash" step. For example, as shown in FIG. 20, first type particles 120 and multiple-particle complexes 100 may be distributed through fluidic channel 1020 such that the particles settle onto one or more of capture spots A1-A4 simultaneously, rather than being translated from spot to spot in a step-wise fashion, as illustrated in FIGS. 11-17. At least one of the specific binding processes, as illustrated in FIGS. 18 and 19, may take place such that certain particles are captured on one or more of capture spots A1-A4. Wash magnet 1910 may then be activated at position M7 for a specific period of time (e.g., one minute) such that unbound first type particles 120 and multiple-particle complexes 100, which have not been specifically bound to one of capture spots A1-A4, are removed from an imaging zone proximate to capture spots A1-A4. For example, for given excitation 1060 provided by light source 1065, configuration of substrate 1012 and settings of imaging system 1050, the imaging zone may be defined as an area that extends less than a micrometer into channel 1020 from the surface of substrate 1012 on which capture spots A1-A4 have been disposed (for example, the extent of evanescent wave propagation beyond substrate 1012 in a total internal reflection mode of illumination through substrate 1012). The removal of unbound first type particles 120 from the imaging zone essentially functions as a "magnetic wash," in which unwanted particles are removed from the imaging zone by magnetic force. The strength of the magnetic field may be tuned such that particles specifically-bound to a capture spot are not removed with the application of the magnetic field from position M7. While four capture spots A1-A4 are shown in FIGS. 10-17 and 20-21, fewer or more capture spots may be used depending on the particular biomolecules of interest.

Figure 22:
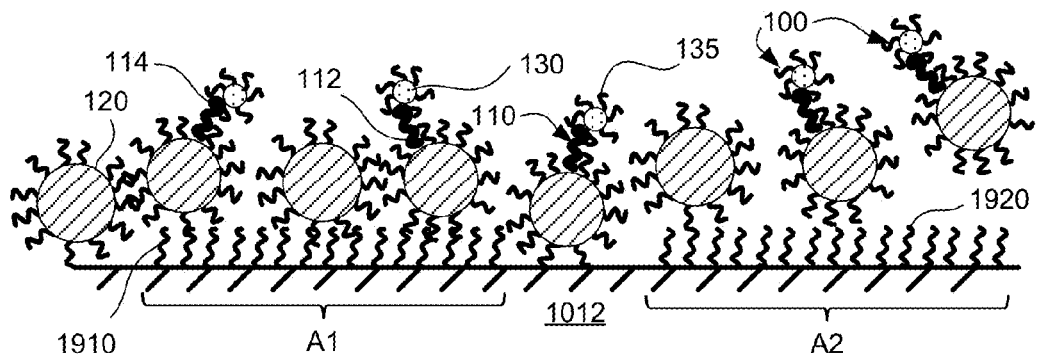
Figure 23:
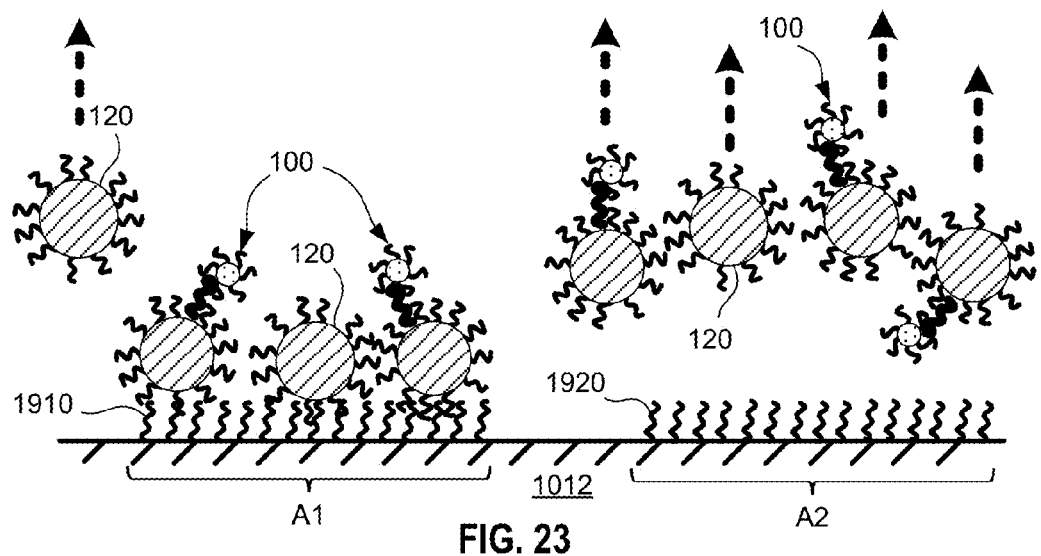
Figure 24:
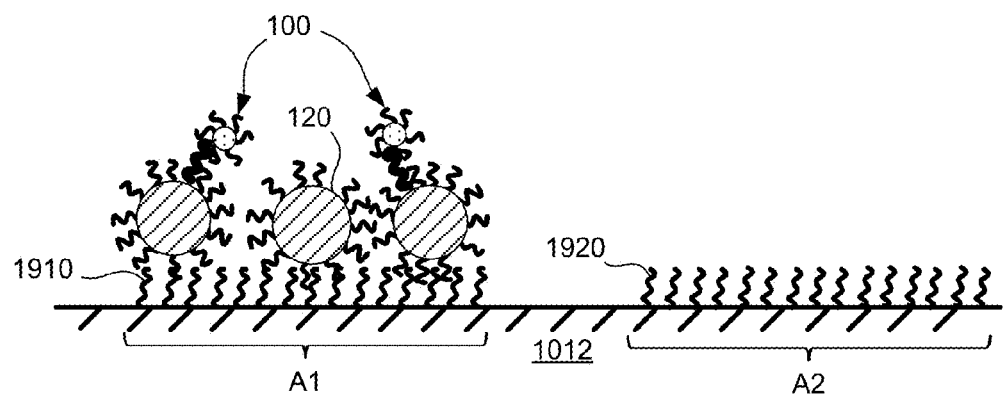

Further details of the magnetic wash step shown in FIG. 18 are illustrated in FIGS. 22-24. The situation shown in FIGS. 22-24 is similar to that shown in FIG. 18 in that first type particles 120 are specifically bound to capture spot A1, while none of the particles in the sample is bound to capture spot A2. Upon application of magnetic force from above (e.g., from a magnet in position M7 as shown in FIG. 21), the unbound particles and multiple-particle complexes are removed from the surface of substrate 1012, as shown in FIG. 23. Provided that the magnetic field strength is not strong enough to remove specifically bound particles, as the magnetic wash step results in specifically bound particles on a capture spot with very low non-specific particle background binding (FIG. 24).

Figure 25:
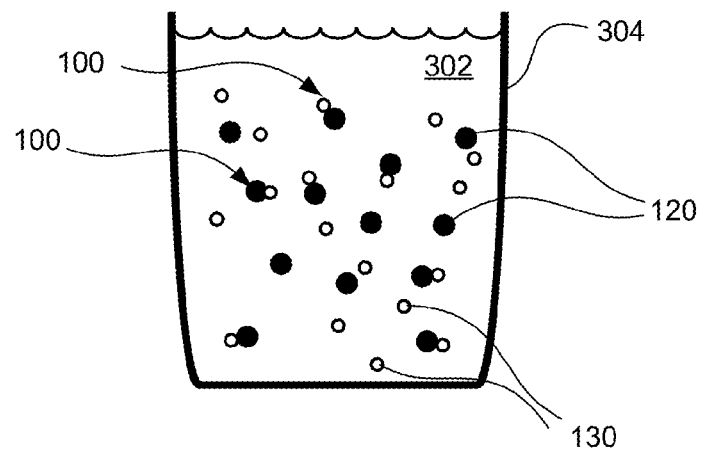
FIGS. 25-27 provide exemplary schematics showing a magnetic sample separation process, in accordance with an embodiment.
Figure 26:
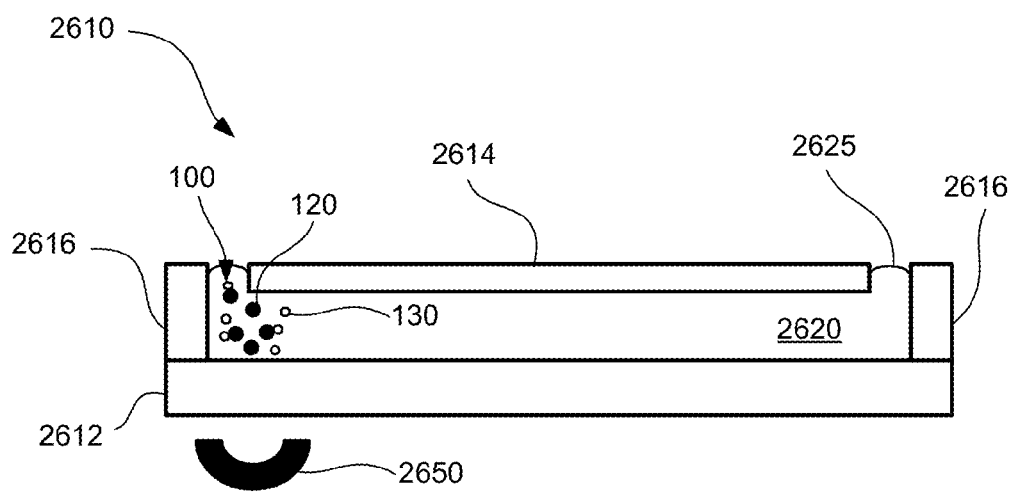
Figure 27:
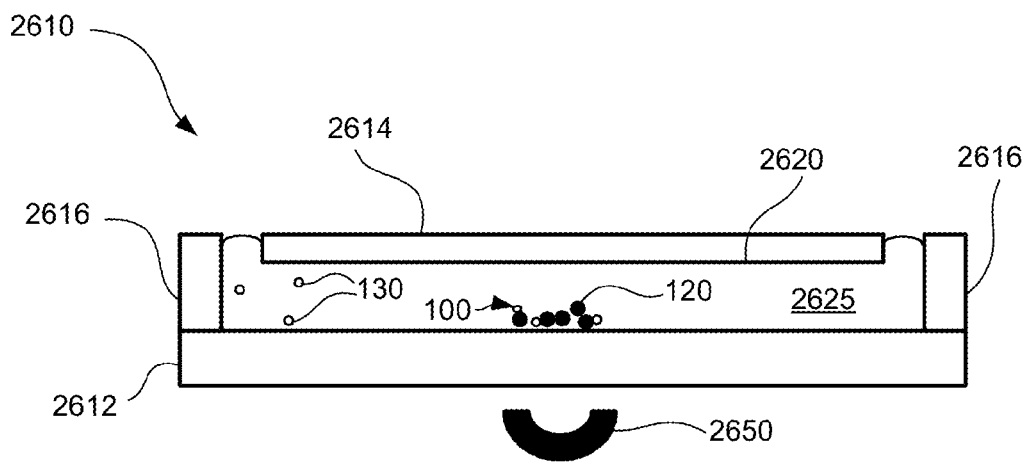

In another embodiment, particle complexes such as those shown in FIGS. 1 and 2 may be separated from free fluorescent particles using a simple mechanical translation. FIGS. 25-27 illustrate an exemplary approach. When a sample, including a target analyte, is introduced to a solution containing functionalized first type particles 120 and functionalized second type particles 130, multiple-particle complexes 100 are formed, as shown in FIG. 25 (FIG. 25 is similar to earlier-described FIGS. 4 and 8). In certain cases, it is necessary to physically separate free functionalized second type particles 130 (e.g., free fluorescent particles) from multiple-particle complexes 100. This separation may be performed by using a cartridge 2610, which is formed of a substrate 2612, an upper component 2614, and a gasket 2616 collectively defining a fluidic chamber 2620. Fluidic chamber 2620 is filled with a buffer 2625. Multiple-particle complex 100, first type particle 120 and second type particle 130 are introduced to fluidic chamber 2620, as illustrated in FIG. 26. For a thin channel device (e.g., channel height<0.2 millimeters), convective mixing is minimal and the cluster of particles generally remains near the inlet port. A magnet 2650 exerts a magnetic force such that field-responsive particles (e.g., first type particle 120 and multiple-particle complex 100) are pulled toward magnet 2650. Translation of magnet 2650 (or activation of electromagnets) may subsequently be used to move multiple-particle complexes 100 and first type particles 120 to a desired location, as shown in FIG. 27. This process provides a physical separation of the confounding free first type particles 120. Multiple-particle complexes 100 at the desired location may then be analyzed by an appropriate detection method, such as fluorescence imaging.

In another embodiment, high index of refraction particles may be used to create enhanced optical detection signals, as illustrated in FIGS. 28-37. For example, a directional luminescent signal enhancement with high index of refraction particle—fluorescent particle complexes may be obtainable. A magnetic particle may act as a high index of refraction spherical lens, which serves to effectively focus illumination radiation onto the luminescent particle. Alternatively, the magnetic particle spherical lens may collect and focus light signal emitted from the luminescent particle.

FIGS. 28-32 show different orientations of multiple-particle complex 100 with respect to an illuminating field 2810, represented by arrows. First type particle 120 may be formed of a combination of materials such that so as to provide a lensing effect, thereby focusing a portion of illuminating field 2810 that is transmitted therethrough. For example, first type particle may be a polystyrene-core particle impregnated or coated with a magnetic component, such as magnetite (Spherotech). Then, the amount of illuminating field 2810 incident on second type particle 130, which may be configured to generate a detectable signal in response to illumination, depends on the orientation of second type particle 130 with respect to first type particle 120. For example, as shown in FIGS. 28-30, when second type particle 130 is "upstream" of first type particle 120 within illuminating field 2810, then second type particle 130 is illuminated in the same way as if it were not part of multiple-particle complex 100. However, the orientation of multiple-particle complex 100 may be such that first type particle 120 focuses illuminating field 2810 away from second type particle 120 (see FIG. 31) such that second type particle 110 receives much less illumination than in the cases shown in FIGS. 28-30. Alternatively, as shown in FIG. 32, second type particle 120 may be within a region in which illuminating field 2810 is focused by first type particle 120 such that second type particle 120 is more intensely illuminated than in other orientations of multiple-particle complex 100.

Additionally, as shown in FIGS. 33-37, the signal generated by second type particle 130 may also be affected by the lensing effects imparted by first type particle 120. Consequently, for the same amount of signal 3310 (indicated by arrows) generated by second type particle 130, the amount of signal 3310 that reaches an observer 3320 depends on the orientation of multiple-particle complex 100. For example, as shown in FIG. 33, when first type particle 120 is directly in the path of signal 3310 between second type particle 130 and observer 3320, first type particle 120 may refract signal 3310 so as to intensify the amount of signal 3310 that reaches observer 3320. Alternatively, multiple-particle complex 100 may be oriented such that first type particle 120 refracts signal 3310 away from observer 3320, thereby reducing the amount of signal 3310 that reaches observer 3320 (see FIGS. 34-37). The focusing and light collection effects are demonstrated experimentally in EXAMPLE VII discussed below.

Both the focusing and light collection effects may be utilized in detection systems to significantly improve the sensitivity of multiple-particle complex detection. When properly oriented relative to a detector (e.g., a CCD or CMOS camera), the measured luminescent signal may be significantly enhanced relative to the signal from an isolated luminescent particle. For instance, multiple-particle complexes may be allowed to tumble in solution. Depending on orientation of the multiple-particle complex relative to the illumination source and detector, this tumbling effect may significantly alter the illumination intensity incident at the luminescent particle. Similarly, during luminescence emission, the magnetic particle spherical lens may serve to focus or direct light in a direction linked to the orientation of the particle complex.

Due to the highly directional nature of the signal enhancement effect illustrated in FIGS. 28-37, tumbling multiple-particle complexes will appear to flash when visualized with an imaging detector such as a CMOS or CCD camera. Free fluorescent particles (i.e., fluorescent particles that are not linked to a magnetic particle in a multiple-particle complex) exhibit no such flash effect, and instead exhibit a steady state fluorescence emission. When attached to magnetic particles in a multiple-particle complex, the flashing particles (when captured in their "bright" orientation) show fluorescence emission that appears to be physically larger and more intense than the free fluorescent particles. Furthermore, particle pairs may be intentionally oriented relative to a detector in order to increase emitted light detection. The particle pairs may be oriented using, for example, magnetic fields and fluid forces.

It may be noted that this localized particle lensing effect is significantly enhanced via the use of high refractive index particles. In an embodiment, magnetic polymer microspheres exhibit an effective index of refraction higher than non-magnetic polymer microspheres. For instance, incorporation of magnetic iron within the microsphere may increase the effective index of refraction of the microsphere, thus yielding stronger focusing effects. For the size range of particles described in this embodiment, the magnetic polymer microspheres give significant signal enhancement relative to non-magnetic polymer microsphere of the same diameter. This signal enhancement effect is experimentally demonstrated in EXAMPLE VIII discussed below.

Several examples of implementations of exemplary embodiments of the present technology are disclosed herein. These descriptive examples are not intended to be limiting, but rather illustrative. Specific quantities and chemicals discussed herein are merely representative, as will be appreciated by those skilled in the art.

EXAMPLE I

Rapid, Specific DNA Target Concentration and Detection

This example of the present technology demonstrates the detection of target DNA using an oligonucleotide sandwich assay and a dual particle capture and detect format. Magnetic particles were functionalized with a 50 nucleotide single stranded DNA capture sequence ("capture probe") specific to a section of the DNA target. The "detect probe" was a 50 nucleotide biotinylated DNA sequence specific to a section of DNA target adjacent to the capture sequence. In the presence of DNA target, the capture and detect probes specifically hybridize to adjacent sections of the target, creating the sandwich. A particle complex is created by adding avidin-functionalized fluorescent particles, which bind to the biotinylated detect probe. Nucleic acid probe sequences are provided in Table 1, and experimental details are provided here. In one instance, target analyte/particle complexes may be delivered to a detection surface via passive sedimentation by ambient gravity. In another approach, target analyte/particle complexes may be delivered to a detection surface via active sedimentation in a centrifuge. In another approach, target analyte/particle complexes may be translated along a two dimensional surface to an analytical region by applying magnetic force from under the two dimensional surface and moving the magnet and thus the particle complexes to the analytical region.

Magnetic particle functionalization. Magnetic particles were coated with an amine-functionalized DNA probe using the following protocol. 100 microliters of a 10 mg/ml solution of 1 micrometer diameter magnetic particles (Dynabead® MyOne Carboxylic Acid, Invitrogen) were transferred to a 1.7 ml micro-centrifuge tube. The tube was placed in a magnetic separator (Invitrogen Dynal) to concentrate the beads to the side wall of the tube. The liquid was removed and particles were re-suspended in water. This wash step was repeated with water and then particles were suspended in 200 microliters of 0.1M MES (2-morpholinoethanesulfonic acid, Fluka), pH 5.2. 100 microliters of 10 mg/ml 1-ethyl-3-[3-dimethylaminopropyl]carbodiimide hydrochloride (EDC, Pierce) and 100 microliters of 10 mg/ml sulfo-N-hydroxysuccinimide (Sulfo-NHS, Pierce) were added to the magnetic particle solution. The solution was mixed for 30 minutes by rotating. The tube was then placed in the magnetic particle separator and the liquid was removed. Particles were then suspended in a 100 microliter solution of 500 micromolar amine-modified capture probe (see Table 1) in 0.1M phosphate buffer, pH 8.0. The solution was mixed for 3 hours at room temperature on a rotator. The tube was then placed in the magnetic separator and the liquid was removed. The particles were washed 3 times with 1×PBS, 0.05% Tween20 (PBST) using the magnetic separator for each step. Particles were then re-suspended in bead buffer ("BB"), which contains 1×PBS, 0.3 molar sodium chloride (NaCl), 20 micrograms/ml herring sperm DNA (Sigma-Aldrich), 200 micrograms/ml bovine serum albumin (BSA, Sigma-Aldrich) and 0.05% Tween20

(Pierce). Concentration of particles at this point was 1 mg/ml. Functionalized particles were stored at 4° C.

Fluorescent particle functionalization. Fluorescent particles (Thermo, Dark Red, 0.39 micrometer, 2% wt/vol) were functionalized by mixing 100 microliters of particle stock solution with 100 microliters of 0.2 mg/ml NeutrAvidin (Pierce) in 0.2 molar sodium phosphate for 4 hours at 4° C. 200 microliters of BB were added. The solution was transferred to a 0.1 micrometer microfiltration centrifuge tube (Millipore) and centrifuged for 8 minutes at 6000 rpm (Fisher Scientific Accuspin Micro17 centrifuge). Particles were re-suspended in bead buffer and the filtration step was repeated two more times (i.e., three washes total). The particles were then re-suspended in bead buffer and stored at 4° C. at a concentration of 0.1% w/v.

Target DNA Capture. Target DNA was captured on capture probe-modified magnetic particles. Biotinylated detect probe was added during hybridization. NeutrAvidin-coated fluorescent particles were added after hybridization to complete the full sandwich.

Synthetic target DNA C05 d100 tar (IDT, Table 1, Example I) is derived from a portion of the influenza H1N1 genome. The capture oligonucleotide (i.e., capture probe) is complementary to the 5'-end of target DNA and was synthesized by Integrated DNA Technologies, Inc. (IDT, Inc.) with a C6-amine 3' modification (capture probe c05 5 pcomp 50 in Table 1). The biotinylated detect oligonucleotide (detect probe) was complementary to the 3'-end of target DNA and was synthesized by IDT, Inc. as the 5' C6-amine derivative (detect probe c05 3 pcomp 50 in Table 1). Biotin was conjugated to this sequence by reaction with Sulfo-NHS-LC-Biotin (Pierce).

Assay protocol. Dilutions of target DNA were mixed with 2E6 capture probe-modified magnetic particles in hybridization buffer ("HB"), (3×SSPE (Saline-Sodium Phosphate-Ethylenediaminetetraacetic acid ("EDTA")) buffer 0.1% sodium dodecyl sulfate ("SDS"), 100 microgram/ml BSA and 20 microgram/ml of herring sperm DNA ("hsDNA")) containing 2 nanomolar biotinylated detect probe and mixed on a rotating heat block at 1100 rpm at 55° C. for 2 hours, allowing formation of the particle/capture probe/target/detect probe complex.

Particle complexes were then washed as follows using a permanent magnet and fluid exchange. Supernatant was removed and particles were re-suspended in 3×SSPE, 0.1% SDS (1×). This was followed by two washes (supernatant exchange) with PBSHT (1×PBS, 500 millimolar NaCl, 2 mg/ml BSA, 20 ug/ml hsDNA, 0.05% Tween20). The particles were then suspended in 100 microliters of PBSHT, and 2E8 NeutrAvidin-fluorescent particles were added. The solutions were mixed on a rotator at room temperature for 15 minutes to allow biotin-NeutrAvidin binding. Magnetic-fluorescent particle complexes are formed in this step, with target DNA forming the link between the particles.

Particle complexes were washed 3× with PBSHT by magnetic isolation and removal of supernatant with final resuspension in 100 microliters of PBSHT. The entire volume of each reaction was transferred to separate wells of a 384 well plate and a bar magnet was used to draw the particle complexes to the bottom surface of the wells This wash procedure removes unbound fluorescent particles so that the only remaining fluorescent particles are those complexed with magnetic particles through interaction with the target.

Figure 38:
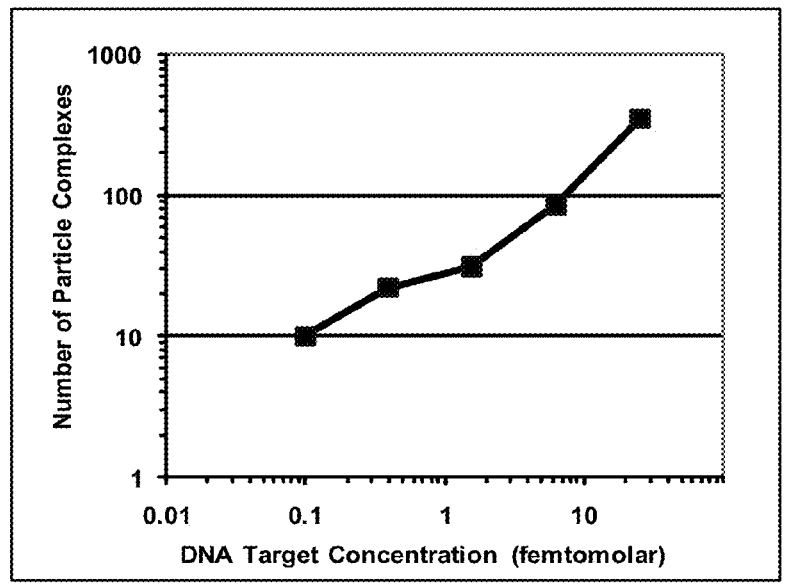
FIG. 38 provides representative results for a DNA target detection experiment (Example I).

Particle complexes were quantified by imaging on an epi-fluorescence microscope (Olympus IX-71) equipped with a 20× objective and Cy5 filters. Particle complexes in the images were counted automatically using a particle counting tool developed in the open-source software ImageJ. Results are presented in FIG. 38, showing the resulting titration curve, with limit of detection at approximately 1 femtomolar target.

In the present example, 1 micrometer diameter magnetic particles were used as an exemplary demonstration. Alternatively, magnetic particles in the diameter size range of 0.01 to 20 micrometers may be used. Alternatively, magnetic particles in the diameter size range of 0.2 to 10 micrometers may be used. Alternatively, magnetic particles in the diameter size range 0.3 to 6 micrometers may be used. It is also noted that magnetic particle size distributions may be monodisperse. Alternatively, a range of magnetic particle sizes may be used simultaneously. It is also noted that non-spherical magnetic particles may be used.

In the present example, commercially available monodisperse polymer shell superparamagnetic particles were used as an exemplary demonstration. Alternative magnetic particle types may be used in this invention. Alternative magnetic particle matrix materials include latex, polystyrene, agarose, and other polymers, silica and silica-based glass compositions, oxides including iron oxides, and ceramics. Magnetic particles may also be composite constructions, such as core-shell particles (e.g., metal or metal oxide core with organic polymer shell), and polymers incorporating metal oxide sub-particles.

In the present example magnetic particle functionalization was performed using amine-modified oligonucletides with EDC-NHS ester chemistry as an exemplary demonstration. Alternative, amine-reactive coupling chemical reactions include those based on isothiocyanates, isocyanates, acyl azides, sulfonyl chlorides, aldehydes, glyoxals, epoxides, oxiranes, carbonates, arylating agents, imidoesters, carbodiimides, and anyhydrides. As an alternative to amine-modified oligonucleotides, thiol-modified oligonucleotides may be used. Alternative thiol-reactive coupling chemical reactions that may be used include those based on haloacetyl and alkyl halide derivatives, maleimides, aziridines, acrylolyl derivatives, arylating agents, and thiol-disulfide exchange reagents. As another alternative to amine-modified oligonucleotides, carboxylate-modified oligonucleotides may be used. Alternative carboxylate-reactive coupling chemical reactions that may be used include diazoalkanes and diazoacetyl compounds, carbonyldiimidazole, and carbodiimides. As another alternative to amine-modified oligonucleotides, hydroxyl-modified oligonucleotides may be used. Alternative hydroxyl-reactive coupling chemical reactions that may be used include epoxides and oxiranes, carbonyldiimidazole, N,N'-disuccinimidyl carbonate, alkyl halogens, isocyanates, or oxidation chemistries. As another alternative to amine-modified oligonucleotides, aldehyde-modified or ketone-modified oligonucleotides may be used. Alternative aldehyde-reactive or ketone-reactive coupling chemical reactions that may be used include hydrazine derivatives, Schiff base formation, reductive amination, and Mannich condensation. As another alternative to amine-modified oligonucleotides, photo-reactive oligonucleotides may be used. Alternative photoreactive coupling chemical reactions that may be used include aryl azides and halogenated aryl azides, benzophenones, diazo compounds, and diazirine derivatives.

In the present example, 0.39 micrometer diameter fluorescent particles were used as an exemplary demonstration. Alternatively, fluorescent particles in the diameter size range of 0.01 to 20 micrometers may be used. Alternatively, fluorescent particles in the diameter size range of 0.2 to 10 micrometers may be used. Alternatively, fluorescent particles in the diameter size range 0.3 to 6 micrometers may be used. It is also noted that fluorescent particle size distributions may be monodisperse. Alternatively, a range of fluorescent particle sizes may be used simultaneously. It is also noted that non-spherical fluorescent particles may be used.

The Dark Red (Thermo) fluorescent particle product used in the example had excitation/emission wavelengths centered at 640/660 nm. An alternative fluorescent dye may be used in the blue part of the spectrum (excitation 360 to 420 nm and emission 420 to 480 nm); green part of the spectrum (excitation 450 to 500 nm, emission 500 to 540 nm); or red part of the spectrum (excitation 540 to 590 nm, emission 590 to 640 nm). Another alternative fluorescent dye may be used in the infrared part of the spectrum, with emission wavelengths>700 nm such as the products from Li-Cor Biosciences. The fluorescent particles used in the present example were based on organic dye fluorophores. Alternative luminophores may be used, including lanthanides such as europium, erbium, and terbium based emitters, as well as semiconductor based emitters, such as quantum dots.

In the present example, the detect probe was a biotinylated oligonucleotide that was subsequently bound to a NeutrAvidin fluorescent particles. Alternatively, the fluorescent particle in this example may be modified with streptavidin or avidin. Alternatively, the fluorescent particle in this example may be coupled directly to the detect oligonucleotide prior to the assay. Alternative fluorescent particle functionalization chemistries are the same as those listed above for magnetic particle functionalization.

The DNA target In the present example was a synthetic 100 nucleotide sequence used as an exemplary demonstration. Alternatively, the DNA target may be any DNA molecule with a minimum length of 30 nucleotides. Alternatively, the DNA target may be 30 to 5000 nucleotides long.

Capture and detect probe lengths used in this example were 50 nucleotides in length with six carbon linkers. Alternatively, oligonucleotide probes may be 10 to 100 nucleotides in length. Alternatively, oligonucleotide probes may be 20 to 70 nucleotides in length.

The hybridization reaction In the present example was performed using a rotating heat block at 1100 rpm at 55° C. for 2 hours as an exemplary demonstration. Alternatively, the hybridization reaction may be performed without mechanical mixing (rotating). Alternatively, the hybridization reactions may be performed in the temperature range 4 to 65° C. Alternatively, the hybridization reactions may be performed in the temperature range 25 to 55° C.

EXAMPLE II

Rapid, Specific RNA Target Detection with Magnetic Concentration to Detection Surface Example II demonstrates detection of RNA target using the methods of Example 1, except that synthetic RNA target (Thermo Scientific, Sequence PrP 1013-27-1, Table 1) was used at 100 picomolar with detect probe at 20 nanomolar.

Magnetic particles used for full sandwich detection were covalently linked with DNA probe (IDT, Table 1, Example II Capture Probe PrP 1013-27-5) as described above. Control magnetic particles were covalently loaded with DNA probe complementary to the 5'-end of the Target RNA (Table 1, Example II Control Probe NA-H1N1-6 3p30). Target hybridizes to the Control Probe particles but does not generate signal because the biotinylated detect probe is also complementary to the 5'-end of the Target RNA. Detect probe complementary to the 5'-end of the target was purchased from IDT with a biotin on the 3'-end and a dT-10 spacer (Table 1, Example II Detect Probe NA-H1N1-6 3p30 biotin).

A total of four different conditions were tested in this experiment: 1) specific capture probe and RNA target (positive sample); 2) mismatch capture probe and RNA target, to look for non-specific hybridization; 3) specific capture probe and no RNA target; and 4) mismatch capture probe and no RNA target. The last two conditions assess non-specific particle-particle interactions.

The assay protocol was as described in Example I. Each particle suspension was transferred to a microplate well and imaged on the inverted fluorescence microscope as described above. No signal was observed in wells with zero RNA or mismatch probes, while the wells with 100 picomolar RNA target and complementary capture and detect probes registered substantial fluorescent bead counts.

The variations described above, with respect to Example I, are also applicable to the present example.

EXAMPLE III

Rapid, Specific DNA Target Detection with Magnetic Concentration, Specific Microarray Surface Capture, and Magnetic Wash Example III demonstrates rapid hybridization followed by selective surface binding to an array of capture spots on a microarray surface. This experiment used the same DNA target sequence, capture probe, magnetic particles and biotinylated probes as in Example I.

Four amine-functionalized probes were spotted onto a custom-activated assay device substrate using a Bio-Dot non-contact microarrayer robot. For this example, the device substrate was a cyclic olefin polymer (COP) planar waveguide, approximately 70 mm×25 mm×1 mm with an integrated light coupling lens. Custom activation was by first performing an oxygen plasma treatment on the COP waveguide followed by silanization with (3-glycidoxypropyl) triethoxysilane to create an amine-reactive surface activated with epoxy groups. Alternative device substrates include transparent planar components made of glass, ceramics, or polymers such as polystyrene or acrylic. Alternative silanization reagents include aminopropyl silanes, aldehyde silanes, vinyl silanes, vinyl sulfone silanes, acrylate silanes, methacrylate silanes, mercapto silanes, hydroxyl silanes, carboxy silanes, azido silanes. Alternatively, surface activation could be via on-surface polymerization or polymer grafting, including with polyethylene glycol polymers with reactive end groups.

Arrays were printed with 3 spots of each probe for a 3×4 array. One of the four surface capture probes was complementary to the probes immobilized on the magnetic particles. The other three surface capture probes were non-complementary mismatches. All surface capture probes were purchased from IDT with 3'-amine linkers and a dT-9 spacer and are listed in Table 1, Example III.

Three samples were prepared in 1.5 ml micro-centrifuge tubes containing 1 milliliter of HB, 1E7 magnetic particles loaded with capture probe as described above, and 5 nanomolar biotinylated detect probe. Target DNA was added to give concentrations of 200 femtomolars and 20 femtomolars. The third sample tube contained no target DNA (zero control).

Samples were mixed for 1 hr at 55° C. on a thermomixer (Eppendorf) at 1200 rpm. Particles were then rinsed once with HB and twice with BB. Particles were then suspended in 90 microliters of BB. 10 microliters of NeutrAvidin-modified fluorescent particles were added for a concentration of 5E8 fluorescent particles per sample. Samples were rotated end-over-end on a rotator (Barnstead/Thermolyne Labquake) for 15 minutes, rinsed two times with BB using magnetic separation, and suspended in approximately 4 microliters of BB.

To perform the assay, a cartridge assembly, similar to that illustrated in FIGS. 10-17, was used. In particular, a plastic microarray substrate was assembled into a plastic fluidic upper component with a pressure sensitive adhesive gasket, defining a fluidic channel above the array. The channel was pre-filled with 100 microliters of BB. Two microliters of sample was added to the inlet of the flow channel. An electromagnet was placed at a location approximately 2 mm upstream of the microarray (e.g., position M0), power to the magnet was turned on to 12V and 200 microliters of BB was added to the inlet. The addition of BB caused flow through the channel, while the magnetic particles were concentrated to the location of the magnet upstream from the microarray (as shown in FIG. 12). The magnet was then turned off and moved to a position directly beneath the first row of spots (C05-TR1SC specific spots; position M1 as shown in FIGS. 10 and 13). The magnet was turned on for approximately 5 seconds at a power of 6V DC (2 amp power supply). The particles migrated over the first row of spots and the magnet was then turned off. After 20 seconds, the magnet was placed under the second row of spots (C18-TR1SC; position M2 as shown in FIGS. 10 and 14) and turned on (6V) for 5 seconds. This procedure was repeated until the particles had been positioned over each row of spots. The slide was then imaged on the fluorescence microscope as in previous experiments.

After initial imaging, a bar-shaped magnet was placed above the microarray (e.g., at position M7 as shown in FIG. 21) for 1 minute. This application of magnetic force functions as a "magnetic wash," as earlier discussed in relation to FIGS. 20-24. That is, magnetic particles that are not specifically bound to an array spot migrate up through channel and out of the imaging zone, thus magnetically washing non-specifically adsorbed particles. The strength of the magnetic field may be tuned such that specifically-bound particles are not removed due to the application of the magnetic field. The cartridge was imaged with an imaging system, then particle pairs at each capture spot per sample were enumerated using image analysis software (ImageJ). The resulting image analysis yielded specific signal on the cognate specific array spots and very little signal on the mismatch spots.

The variations described above, with respect to Example I, are also applicable to the present example.

EXAMPLE IV

Rapid, Specific RNA Target Detection with Waveguide-Based Fluorescence Detection In this example, specific particle complex detection is demonstrated in the context of a planar waveguide based detection system. The materials and general method used in this experiment were the same as those described in Example II. Three samples were run: 1) a 10 picomolar target sample; 2) a 100 femtomolar target sample; and 3) a zero target control. As in other experiments, the zero target control had very few particle pairs when imaged in the bottom of a microtiter plate well on microscope. The 10 picomolar target sample was then used to test capture of the particle pairs on a microarray. The microarray included 3 different capture probes, as described in Table 1, Example IV.

Figure 39:
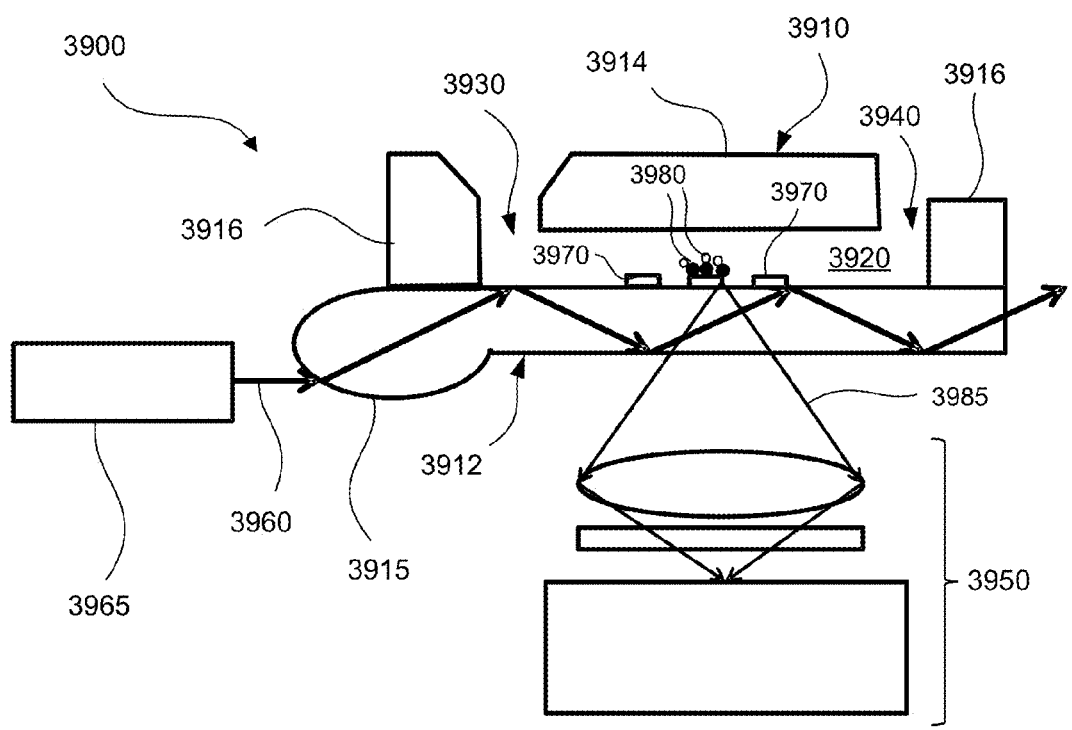
FIG. 39 provides an exemplary schematic for a sample processing and analyte detection system, in accordance with an embodiment.

The slide was imaged with waveguide illumination using the apparatus shown schematically in FIG. 39. As shown in FIG. 39, a sample preparation and detection system 3900 includes a cartridge assembly 3910, which includes a planar waveguide 3912, with a refractive volume 3915, an upper component 3914, and gasket 3916 defining a fluidic channel 3920. Fluidic channel 3920 includes an inlet port 3930 and an outlet port 3940. System 3900 further includes an imaging system 3950, which may in turn include, for example, one or more refractive elements, diffractive elements, reflective elements, filters and sensors. System 3900 also includes excitation energy 3960 (represented by an arrow) provided by an excitation source 3965. Excitation source 3965 may be, for instance, a laser, an LED or other suitable source of excitation energy. As shown in FIG. 39, an array of capture spots 3970 is affixed to a surface of planar waveguide 3912 within fluidic channel 3920 such that target analyte (or multiple-particle complexes 3980 containing the target analyte) may be captured at one or more capture spots 3970. In experiment, particle complexes were only detected on the specific NA-H1N1-6 3p30 COMP-NH2 spots.

The variations described above, in reference to Examples I and III, are also applicable to the present example.

EXAMPLE V

Multiplexed Rapid, Specific DNA Target Detection with Specific Microarray Capture In another embodiment, a cocktail of particle pairs is added to a sample containing a plurality of different target analytes. Target analyte/particle complexes are added to a flow chamber including an array of capture spots specific for different particle probes, as described in Example IV. Signal measured on the capture spots indicate the presence and amount of target analyte in the original solution.

This example demonstrates the use of a cocktail of functionalized particles in the context of target detection. A cocktail of particles were prepared with probes for four possible nucleic acid targets (see Table 1, Example V). For each potential target, the cocktail contained magnetic particles with specific capture probe and a biotinylated detect probe. Each magnetic particle type was at a concentration of 2E+06 particles/ml and each biotinylated probe was at 10 nanomolar concentration. Thus, there were four magnetic bead capture sequence types and four biotinylated detect sequence types, for a total of eight different probe sequences in the cocktail.

Substrates were prepared by printing a microarray with sequences complementary to the probes on the magnetic particles (sequences provided in Table 1; capture configuration shown in FIG. 18).

Figure 40:
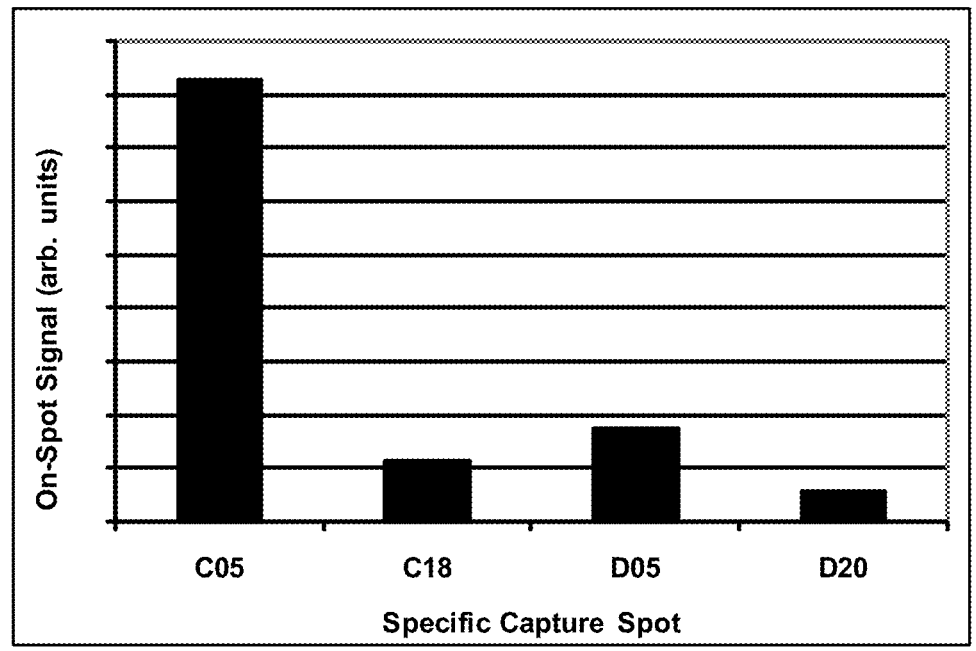
FIG. 40 provides exemplary results for the multiplexed particle experiment described in Example V.

The assay was performed by adding one (sequence C05) of the four possible targets at a concentration of 100 femtomolars. Assay steps and microarray were same as in Example III. The processed substrate was imaged using a fluorescent microscope and particle complexes were enumerated using image analysis software (Image J). Representative results are provided in FIG. 40. Results show that signal is strongest on the correct complementary spot. Mismatch spots show minimal signal relative to off-spot background.

The variations described above, with respect to Examples I and III, are also applicable to the present example.

EXAMPLE VI

Detection of Protein Target Using Particle Complex Approach

This example demonstrates that the system may be used to detect protein targets. In this example the target is an antibody. 200 microliters of Dynabeads MyOne Streptavidin T1 (Life Technologies) were rinsed with 100 millimolar phosphate, with pH of 7.2, using magnetic separation in a 1.7 ml micro-centrifuge tube, and then suspended in 200 microliters of phosphate buffer with a pH of 7.2. 20 microliters of 1 mg/ml biotinylated donkey anti-rabbit IgG was added to the particles, which were mixed for 1 hour on a thermomixer at room temperature and 900 rpm. Particles were then rinsed four times with PBT (1×PBS, 10 mg/ml BSA, 0.05% Tween 20) using magnetic separation.

100 microliters of fluorescent particles (Duke Sci., FR3040PA, 0.39 um Dark Red Fluorescent polystyrene, 2% w/v) were loaded with 20 ul of a mixture of ovalbumin (OVA) and bovine serum albumin (BSA) at a 1:5 ratio (1 mg/ml OVA:5 mg/ml BSA). The OVA/BSA solution was added to the particles and the mixture was incubated overnight at 4° C., then rinsed four times over a 0.1 micrometer spin filter (Amicon) with PBT. For each rinse, 400 microliters of PBT buffer were added and the filter tube was centrifuged at 5000 rpm for 5 min. Flow through was discarded and another 400 microliters of PBT buffer were added to the upper chamber containing the particles. Particles were then suspended in 200 microliter PBT to yield a 1% w/v suspension.

The analyte for this assay was rabbit anti-ovalbumin IgG. 1:4 serial dilutions of rabbit anti-ovalbumin were prepared in BB to make target solutions of 128, 32, 8, 2, 0.5 and 0 pg/ml.

Figure 41:
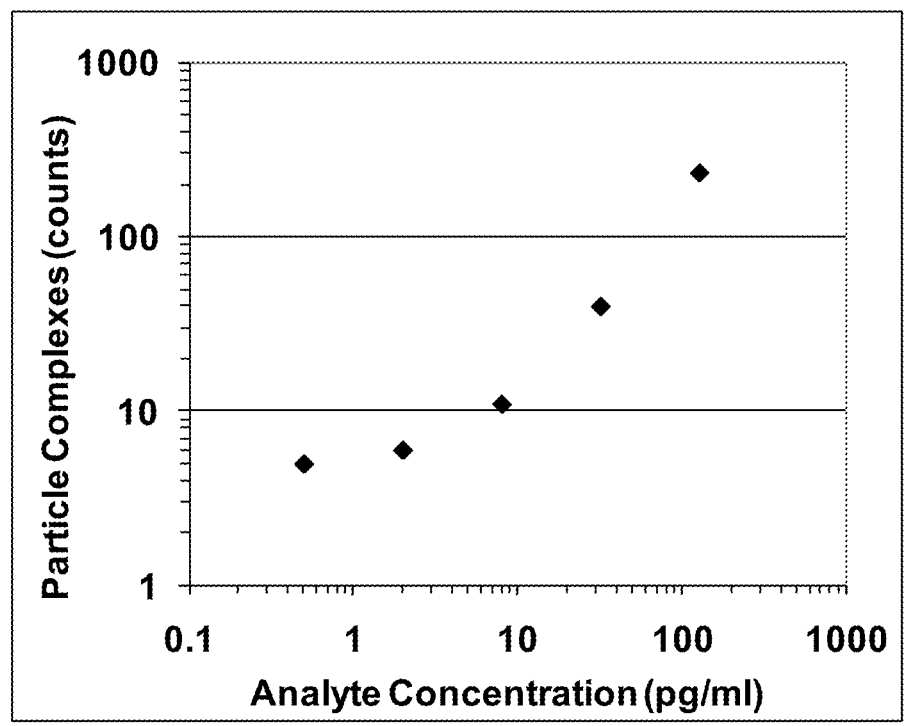
FIG. 41 provides exemplary results for the protein detection experiment described in Example VI.

Assay steps. 1 microliter of magnetic particles (10 mg/ml stock) was added to each 800 microliter sample in a 1.7 ml micro-centrifuge tube. The samples were mixed for one hour at room temperature (Barnstead/Thermolyne labquake). Particles were then separated via magnetic separation and supernatant removed. 100 microliters of BB were added and 10 microliters of a 1:10 dilution of ovalbumin modified fluorescent particles were added, and the reaction was mixed on a rotator for 15 minutes. 200 microliters of BB were added, and the tubes were placed in a magnetic separator and 99% of the supernatant was removed. 200 microliters of BB were then added and samples were transferred to a 96-well plate. A hand-held magnet was used to concentrate the magnetic particles and magnetic particle-fluorescent particle pairs on the bottom of the well. Sample wells were then imaged on a fluorescent microscope. Representative results are provided in FIG. 41. This preliminary experiment shows a detection limit of approximately 10 picograms/ml antibody target.

In the present example, 1 micrometer diameter magnetic particles were used as an exemplary demonstration. Alternatively, magnetic particles in the diameter size range of 0.01 to 20 micrometers could be used. Alternatively, magnetic particles in the diameter size range of 0.2 to 10 micrometers could be used. Alternatively, magnetic particles in the diameter size range 0.3 to 6 micrometers could be used. It is also noted that magnetic particle size distributions may be monodisperse. Alternatively, a range of magnetic particle sizes could be used simultaneously. It is also noted that non-spherical magnetic particles could be used.

In the present example, commercially available monodisperse polymer shell superparamagnetic particles were used as an exemplary demonstration. Alternative magnetic particle types could be used in this invention. Alternative magnetic particle matrix materials include latex, polystyrene, agarose, and other polymers, silica and silica-based glass compositions, oxides including iron oxides, and ceramics. Magnetic particles may also be composite constructions, such as core-shell particles (e.g., metal or metal oxide core with organic polymer shell), and polymers incorporating metal oxide subparticles.

In the present example magnetic particles were functionalized with streptavidin to provide immobilization of biotinylated antibodies. Several alternatives to biotin-streptavidin binding could be used for protein-particle conjugation. Alternative, amine-reactive coupling chemical reactions include those based on succinimidyl esters, such as NHS, isothiocyanates, isocyanates, acyl azides, sulfonyl chlorides, aldehydes, glyoxals, epoxides, oxiranes, carbonates, arylating agents, imidoesters, carbodiimides, and anyhydrides. Alternative thiol-reactive coupling chemical reactions that could be used include those based on haloacetyl and alkyl halide derivatives, maleimides, aziridines, acrylolyl derivatives, arylating agents, and thiol-disulfide exchange reagents. Alternative carboxylate-reactive coupling chemical reactions that could be used include diazoalkanes and diazoacetyl compounds, carbonyldiimidazole, and carbodiimides. Alternative hydroxyl-reactive coupling chemical reactions that could be used include epoxides and oxiranes, carbonyldiimidazole, N,N'-disuccinimidyl carbonate, alkyl halogens, isocyanates, or oxidation chemistries. Alternative aldehyde-reactive or ketone-reactive coupling chemical reactions that could be used include hydrazine derivatives, Schiff base formation, reductive amination, and Mannich condensation. Alternative photoreactive coupling chemical reactions that could be used include aryl azides and halogenated aryl azides, benzophenones, diazo compounds, and diazirine derivatives.

In the present example, 0.39 micrometer diameter fluorescent particles were used as an exemplary demonstration. Alternatively, fluorescent particles in the diameter size range of 0.01 to 20 micrometers could be used. Alternatively, fluorescent particles in the diameter size range of 0.2 to 10 micrometers could be used. Alternatively, fluorescent particles in the diameter size range 0.3 to 6 micrometers could be used. It is also noted that fluorescent particle size distributions may be monodisperse. Alternatively, a range of fluorescent particle sizes could be used simultaneously. It is also noted that non-spherical fluorescent particles could be used.

The Dark Red (Thermo) fluorescent particle product used in the example had excitation/emission wavelengths centered at 640/660 nm. An alternative fluorescent dye could be used in the blue part of the spectrum (excitation 360 to 420 nm and emission 420 to 480 nm); green part of the spectrum (excitation 450 to 500 nm, emission 500 to 540 nm); or red part of the spectrum (excitation 540 to 590 nm, emission 590 to 640 nm). Another alternative fluorescent dye could be used in the infrared part of the spectrum, with excitation wavelengths (emission>700 nm) such as the products from Li-Cor Biosciences. The fluorescent particles used In the present example were based on organic dye fluorophores. Alternative luminophores could be used, including lanthanides such as europium, erbium, and terbium based emitters, as well as semiconductor based emitters, such as quantum dots.

In the present example, fluorescent particles were modified via physical adsorption of protein to the particles. Alternatively, protein can be covalently attached to the fluorescent particles via the coupling chemistries described for the magnetic particles as listed above.

EXAMPLE VII

Demonstration of Particle Complex Enhanced Fluorescence Effect

This experiment demonstrates the directional enhancement of fluorescent particle signal in the context of a particle complex. The experiment is similar to that described in Example II, with the exception that larger diameter particles were used to enable better microscopic observation and slower Brownian motion. Magnetic particles were 5.9 micrometer diameter particles from Spherotech. Fluorescent particles were 0.39 micrometer diameter Duke Scientific Dark Red particles labeled with NeutrAvidin, as described in previous Examples.

1 nanomolar RNA target was captured with the previously described magnetic particle—biotinylated detect probe sandwich. Particle complexes were rinsed three times and incubated with NeutrAvidin fluorescent beads and rinsed before imaging on the microscope as described in Example II. In order to foster particle motion, a hand held permanent magnet was slowly waved back and forth near the well being imaged. This gave tumbling motion in the well that led to the flashing effect.

Figure 42:
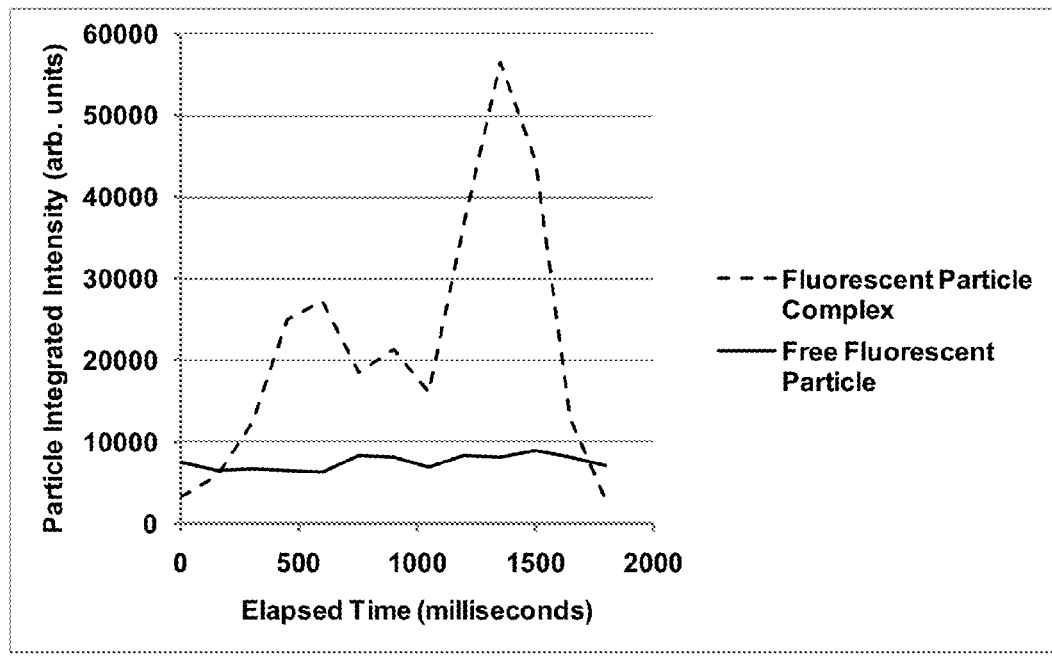
FIG. 42 provides representative experimental results demonstrating fluorescence signal enhancement resulting from alignment of particle complexes, as described in Example VII.

Microscopic video capture (Olympus IX-71 fluorescence microscope with a Retiga cooled CCD camera) was performed during tumbling at a frame rate of approximately 7 frames per second. A video field of view was then selected that included both a free fluorescent particle and a fluorescent particle linked to a magnetic particle. Within an individual image frame, image analysis software (Image J) was used to calculate integrated intensity (i.e., sum of individual pixel intensities over fluorescent particle area) for one free fluorescent particle and the one particle linked to a magnetic particle undergoing tumbling motion. Thirteen consecutive frames were analyzed in this manner. The resulting integrated intensity versus time plot is provided in FIG. 42. It was observed that the linked particle shows a very large intensity increase as the fluorescent particle-magnetic particle pair rotates through different orientations relative to the detector (e.g., as shown in FIGS. 28-37). A large increase in integrated intensity is followed by a decrease in intensity then another increase and finally a decrease over time. In contrast, the free fluorescent particle shows relatively constant fluorescence intensity over time, as expected. One may readily envision how thresholding analysis may be used to distinguish between free fluorescent particles and magnetic-fluorescent particle complexes.

The variations described above, with respect to Example I, are also applicable to the present example.

EXAMPLE VIII

Demonstration of High Index of Refraction Particle Advantage

The particles described in Example VII were used to in a similar experiment to compare fluorescence intensities of free fluorescent particles, magnetic particle—fluorescent particle complexes, and non-magnetic particle—fluorescent particle complexes. For the latter case, a 6 micrometer diameter polymer microspheres were functionalized with capture probe as described for the magnetic microspheres in Example II. The RNA target assays were performed as previously-described in Example II. No multiple-particle complex was observed in the zero-target control, as expected. Multiple-particle complexes were observed in both the 1 picomolar and 10 picomolar target wells. Evidence of the enhanced fluorescence effect is presented by quantitatively measuring the fluorescence signal for oriented particle complexes and free fluorescent particles. Images were collected on an Olympus IX-71 fluorescence microscope with a Retiga cooled CCD camera. For a given camera gain and exposure, the free fluorescent particles showed a fluorescence signal of approximately 600 relative fluorescence units ("RFU"), reported as average pixel intensity over the particle project area (Image J analysis). In contrast, when magnetic particle—fluorescent particle complexes are oriented in their "brightest" alignment, signal intensity saturates the 12-bit camera. The oriented particle complex fluorescence is therefore at least 7 times more intense than the free fluorescent particle counterpart. In contrast, non-magnetic particle—fluorescent particle complexes did not show the fluorescence enhancement in any orientation.

The variations described above, with respect to Example I, are also applicable to the present example.

EXAMPLE IX

Detection of In Vitro Transcribed RNA

Figure 43:
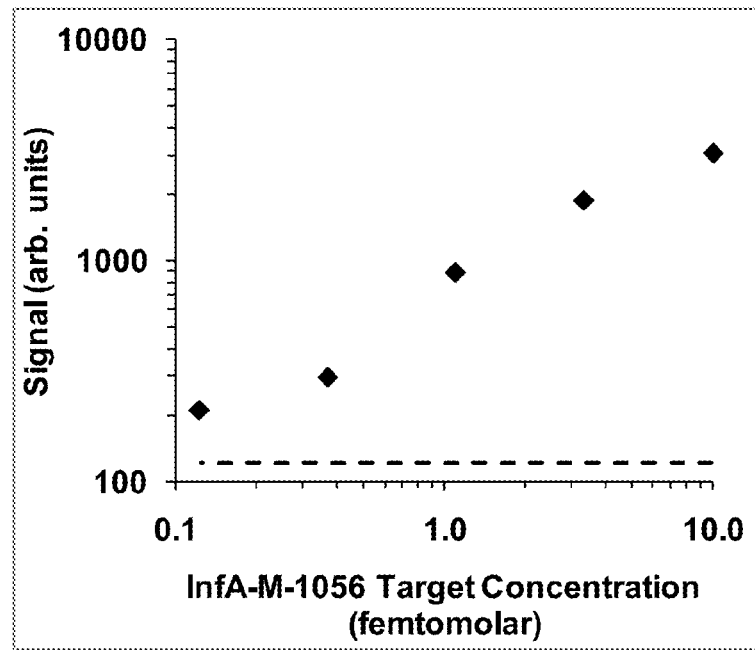
FIG. 43 provides exemplary results for the RNA detection experiment described in Example IX.

In this example, direct detection of an RNA molecule of 1056 bases transcribed from an in vitro reaction is demonstrated. A plasmid containing a sequence from Influenza A Matrix gene flanked with T7 RNA polymerase promoter was constructed such that it became the template for transcription of a 1056 base RNA (InfA-M-1056). The RNA transcript was synthesized using a commercially available kit (Qiagen) and quantified by UV-vis spectroscopy. The materials and general method used in the detection experiment were the same as those described in Example II. Serial dilution of the stock InfA-M-1056 RNA was made to generate test solutions of 10, 3.3, 1.1, 0.37, 0.12, and 0 femtomolar target molecule in a set of reactions. Signal above zero target was measured at the lowest concentration, demonstrating direct detection of a large RNA molecule to sub-femtomolar concentration, as shown in FIG. 43.

The variations described above, with respect to Example I, are also applicable to the present example.

EXAMPLE X

Detection of Specific RNA from Viral Cell Culture Supernatant

Figure 44:
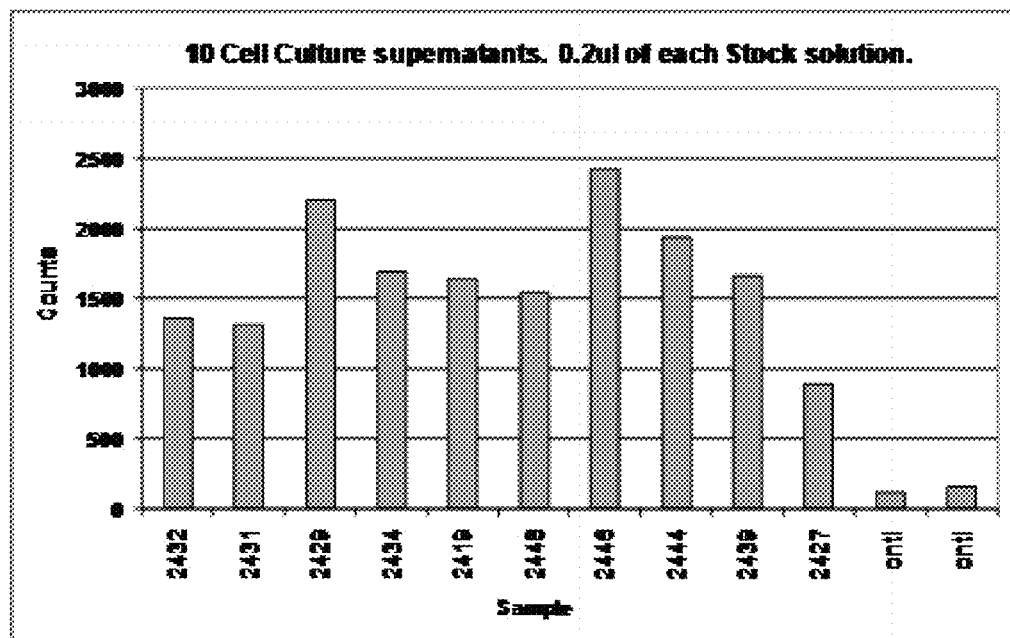
FIGS. 44 and 45 provide exemplary results for the RNA detection experiment described in Example X.
Figure 45:
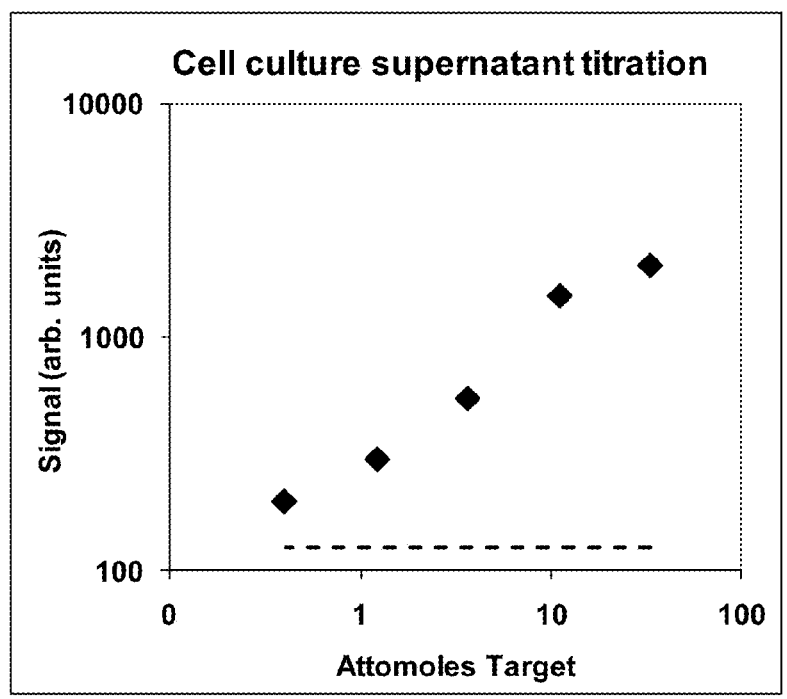

In this example, direct detection of specific RNA target sequences from viral cell culture supernatants is demonstrated. Cell cultures were prepared with 10 strains of Influenza A, and total RNA was harvested by standard methods. The materials and general method used in the detection experiment were the same as those described in Example II. The quantity of specific sequence RNA corresponding to the Matrix gene, as detailed in Example IX, was measured by a RT-PCR quantitation assay using the IVT-RNA InfA-M-1056 as reference standard. 0.2 microliters of the 15 microliter aliquots for ten of the supernatants were tested, all registering signal well above the zero target controls. FIG. 44 shows the number of particle complexes (i.e., counts) for ten viral supernatants derived from clinical influenza samples, numbered 2427-2432. Zero target control samples are indicated as "cntl" on the plot. Based on the quantitation data, the number of target molecules per reaction ranged from 3.8E6 to 1E7, or 12.6 to 33 femtomolars. Counts were in the 100's to 1000's, representing orders of magnitude excess sensitivity. Serial dilution was performed on one sample (See FIG. 45), showing measurable counts above zero target controls to target concentration of 2.4E5 molecules, or ~100 attomolars.

The variations described above, with respect to Example I, are also applicable to the present example.

EXAMPLE XI

High Sensitivity Detection of HIV p24 Antigen with Enhanced Magnetic Separation

This example demonstrates high sensitivity detection of a viral protein antigen in an antibody sandwich format, utilizing a magnetic separation device to isolate fully formed two-bead complexes. Monoclonal antibodies to HIV p24 protein were covalently functionalized to magnetic beads via NHS/EDC coupling chemistry. Briefly, 2.5E8 COOH-magnetic beads (Life Tech) were activated by mixing with equal volumes of 10 mg/ml sulfo-N-Hydroxysuccinimide (SNHS; Pierce) and 10 mg/ml 1-ethyl-3-(3-dimethylaminopropyl) carbodiimide (EDC; Aldrich) in 0.1 molar MES buffer for 30 minutes at 25° C., followed by rinsing and resuspension in 1×PBS+0.05% tween20 (PBST). 20 micrograms of monoclonal Mouse anti p24 antibody were added and mixed at 25° C. for 1 hour. 100 micrograms of Bovine Serum Albumin (BSA; Sigma) were added and mixed for 30 minutes, followed by three magnetic rinses with 100 microliters PBST+ 1% BSA. NeutrAvidin (Pierce) was adsorbed to fluorescent beads as described in Example I (NA-F beads). A second anti-HIV p24 monoclonal antibody was biotinylated by chemical functionalization with sulfo-NHS-LC-biotin (Pierce). Serial dilutions of p24 antigen (Meridian) were added to mixtures of 1E7 anti-p24 magnetic beads with 0.5 microgram of biotinylated anti-p24 antibody in 1×PBS+ 0.05% tween20+90% Fetal Calf Serum (PTS), and incubated at 25° C. with rotation for 25 minutes. The samples were washed three times in BB by magnetic separation, and 18 microliters of 0.2% NA-Fl beads were added followed by 10 minutes incubation at 25° C.

A flow cell was constructed using a proprietary waveguide substrate. The flow cell was placed in a first position over a magnet arrangement such that introduction of the beads/target mixture would cause immobilization of substantially all of the multiple-particle complexes (i.e., complex formed by linked magnetic bead, target analyte, and fluorescent bead combinations) and magnetic beads in the flow cell over the magnet, while unbound fluorescent beads would flow through and away from the magnetic zone. Then, the flow cell was translated relative to the magnet arrangement in a translation direction orthogonal to the direction of the liquid flow in the fluidic channel of the flow cell, so that substantially all of the multiple-particle complexes and magnetic beads are moved across the floor of the flow cell into an imaging zone, as conceptually illustrated in FIGS. 25-27. Movement of the multiple-particle complexes by magnetic translation separates substantially all the bead complexes from remaining free unbound fluorescent beads.

Figure 46:
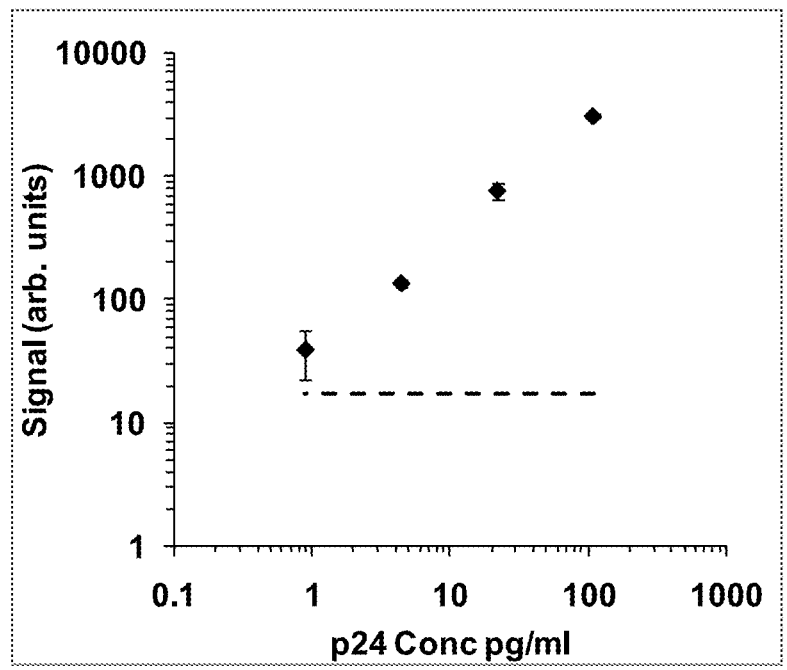
FIGS. 46 and 47 provide exemplary results for the HIV p24 antigen detection experiment described in Example XI.
Figure 47:
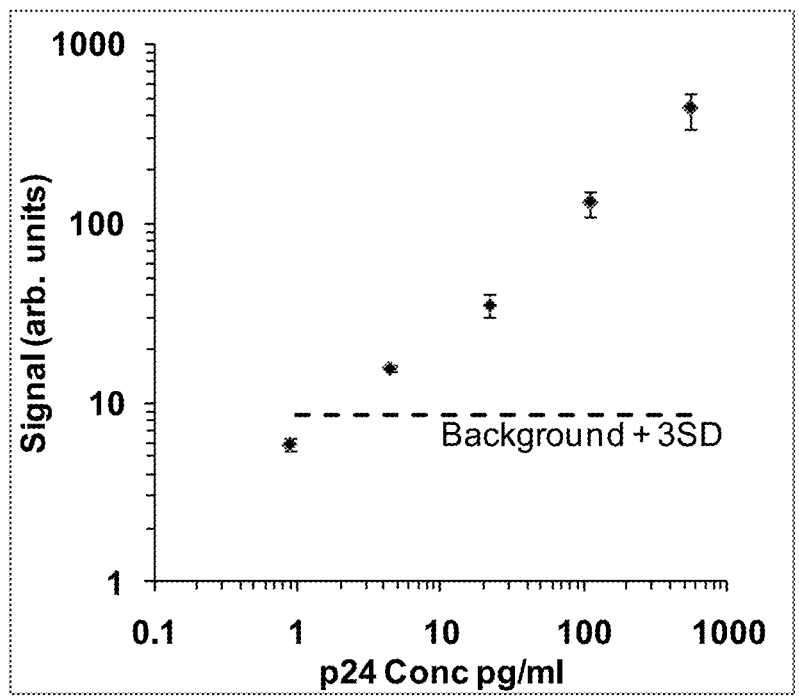

The flow cell was positioned in a primary position of the magnet arrangement, and each of the p24 detection mixtures was transferred into the entry ports of the flow cell device. The flow cell was translated at ~1 mm/second into a secondary position, and the resulting multiple-particle complexes were imaged on a fluorescence microscope and counted by custom Image) macros as described in previous examples (See FIG. 46). Then the fluorescent beads of the fully formed complexes were imaged by waveguide illumination on a custom diode laser/camera reader device, and the integrated fluorescent signal was recorded (See FIG. 47). In bead counting mode, signal at the lowest target concentration was well above the zero target control signal. Using the integrative mode resulted in lower gross signal, thus the first data point above three standard deviations above background was 4.4 picograms per milliliter.

The variations described above, with respect to Example I, are also applicable to the present example.

Changes may be made in the above methods and systems without departing from the scope hereof. It should thus be noted that the matter contained in the above description or shown in the accompanying drawings should be interpreted as illustrative and not in a limiting sense. The following claims are intended to cover generic and specific features described herein, as well as statements of the scope of the present method and system, which, as a matter of language, might be said to fall therebetween.

Although each of the aforedescribed embodiments have been illustrated with various components having particular respective orientations, it should be understood that the system as described in the present disclosure may take on a variety of specific configurations with the various components being located in a variety of positions and mutual orientations and still remain within the spirit and scope of the present disclosure. Furthermore, suitable equivalents may be used in place of or in addition to the various components, the function and use of such substitute or additional components being held to be familiar to those skilled in the art and are therefore regarded as falling within the scope of the present disclosure. Therefore, the present examples are to be considered as illustrative and not restrictive, and the present disclosure is not to be limited to the details given herein but may be modified within the scope of the appended claims.

TABLE 1

| DESCRIPTION | SEQUENCE NAME | SEQUENCE |
| --- | --- | --- |
| EXAMPLE I | | |
| Target DNA (100 mer) | C05 d100 tar | 5'-TCC AAC GTG AAG AAT CTG TAT GAG AAA GTA AAA AGC CAA TTA AAG AAT AAT GCC AAA GAA ATA G- GA AAC GGG TGT TTT GAA TTC TAT CAC AAG TGT AAC G-3' |
| Detect Probe (biotinylated) | c05 3pcomp 50 | 5'-(C6NH2)-TTT TTT TTT CGT TAC ACT TGT GAT AGA ATT CAA AAC ACC CGT TTC CTA TTT CTT TGG CA-3' |
| Capture Probe (on magnetic bead) | c05 5pcomp 50 | 5'-TTT AAT TGG CTT TTT ACT TTC TCA TAC AGA TTC TTC ACG TTG GAT-(C6NH2)-3' |
| EXAMPLE II | | |
| Target RNA (60 mer) | PrP 1013-27-1 | 5'-UGC AGG ACU UUC UUU CUA ACU CAA GGG GCC UUG UUG AAU GAC AAG CAU UCC AAU GGA ACC G-3' |
| Capture Probe (Magnetic bead) | PrP 1013-27-5 | 5'-(C6NH2)-TTT TTT TTT TCG GTT CCA TTG GAA TGC TTG TCA TTC AAC A-3' |

TABLE 1-continued

| DESCRIPTION | SEQUENCE NAME | SEQUENCE |
| --- | --- | --- |
| Control Probe (Magnetic bead) | NA-H1N1-6 3p30 | 5'-GGC CCC TTG AGT TAG AAA GAA AGT CCT GCA TTT TTT TTT TT-(C6NH2)-3' |
| Detect Probe | NA-H1N1-6 3p30 biotin | 5'-GGC CCC TTG AGT TAG AAA GAA AGT CCT GCA TTT TTT TTT TT-Biotin-3' |

EXAMPLE III
Target sequence, Magnetic bead probe and biotinylated detect probes were the same as in Example I.

Surface Capture Probes:

| Surface capture probe complementary to magnetic bead | C05-TR1SC | 5'-CCAACGTGAAGAATCTGTATGAGAAAGTAAAAAGTTTTTTTTT-(C6NH2)-3' |
| --- | --- | --- |
| Non-specific surface capture probes: | C18-TR1SC | 5'-GAA AAT ACA ACA ATC TGG ACT AGT GTTTTTTTT-(C6NH2)-3' |
| | D05-TR1SC | 5'-CCT GGA GAA CCA ACA TAC AAT TGATTTTTTTT-(C6NH2)-3' |
| | D20-TR1SC | 5'-TCA TGG AGT GAA AGG CTG GGC CTT TGATGA TTTTTTTTT-(C6NH2)-3' |

EXAMPLE IV
Target sequence, Magnetic bead probe and biotinylated detect probes were the same as in Example II Surface Capture Probes:

| | NA-H1N1-6 3p30 COMP-NH2 | 5'-(C6NH2)-TTT TTT TTT TGT TGA ATG ACA AGC ATT CCA ATG AAA CCG-3' |
| --- | --- | --- |
| | FRANC-174-NH2 | 5'-Amine-GCC ACC TTT AAT CCA CAG-3' |
| | RNDM-NH2 | 5'-Amine- ATT CGT GGC AAG TTC TCA G-3' |

EXAMPLE V
Target sequence, Magnetic bead probe and biotinylated detect probes were the same as in Example I.

Surface Capture Probes:

| Surface capture probe complementary to magnetic bead probe: | C05-TR1SC | 5'-CCAACGTGAAGAATCTGTATGAGAAAGTAAAAAGTTTTTTTTTT-(C6NH2)-3' |
| --- | --- | --- |
| Non-specific surface capture probes: | C18-TR1SC | 5'-GAA AAT ACA ACA ATC TGG ACT AGT GTTTTTTTT-(C6NH2)-3' |
| | D05-TR1SC | 5'-CCT GGA GAA CCA ACA TAC AAT TGATTTTTTTT-(C6NH2)-3' |
| | D20-TR1SC | 5'-TCA TGG AGT GAA AGG CTG GGC CTT TGATGA TTTTTTTTT-(C6NH2)-3' |

Microarray Surface Capture Probes:

| Surface Capture Probe | C05-TR1SC | 5'-CCAACGTGAAGAATCTGTATGAGAAAGTAAAAAGTTTTTTTTTT-Amine-3' |
| --- | --- | --- |
| | C18-TR1SC | 5'-GAA AAT ACA ACA ATC TGG ACT AGT GTTTTTTTTT-Amine-3' |
| | D05-TR1SC | 5'-CCT GGA GAA CCA ACA TAC AAT TGATTTTTTTTT-Amine-3' |
| | D20-TR1SC | 5'-TCA TGG AGT GAA AGG CTG GGC CTT TGATGA TTTTTTTTT-Amine-3' |

Magnetic Particle Capture Probes:

| Capture Probe (on magnetic bead) | C05-TR1 | 5'-TTT AAT TGG CTT TTT ACT TTC TCA TAC AGA TTC TTC ACG TTG GAT-Amine-3' |
| --- | --- | --- |
| | C18-TR1 | 5'-CAC TAG TCC AGA TTG TTG TAT TTT CTTTTTTTT-Amine-3' |
| | D05-TR1 | 5'-TCA ATT GTA TGT TGG TTC TCC AGGTTTTTTTT-Amine-3' |

TABLE 1-continued

| DESCRIPTION | SEQUENCE NAME | SEQUENCE |
| --- | --- | --- |
| | D20-TR1 | 5'-ATC ATC AAA GGC CCA GCC TTT CAC TCCATG ATTTTTTTTT-Amine-3' |
| Biotinylated Detect Probes: | | |
| Detect Probes | C05-TR2 | 5'-Biotin-TTTTTTTTTCCT ATT TCT TTG GCA TTA TTC TTT AAT TGG-3' |
| | C18-TR2 | 5'-Biotin-TTTTTTTTTACG CCA CAA AAA GAA ATG CTG CTC C-3' |
| | D05-TR2 | 5'-Biotin-TTTTTTTTTAAC AGT TTG TTC ATT TCT GAG TCA GTT AGA-3' |
| | D20-TR2 | 5'-Biotin-TTTTTTTTTATC GTT CTT CCC ATC CAC ACG TCA TTT CC-3' |
| Synthetic DNA Target: | | |
| Target DNA (100 mer) | C05 Target | 5'-TCC AAC GTG AAG AAT CTG TAT GAG AAA GTA AAA AGC CAA TTA AAG AAT AAT GCC AAA GAA ATA GGA AAC GGG TGT TTT GAA TTC TAT CAC AAG TGT AAC G-3' |

What is claimed is:

1. A system for sample preparation and analyte detection, the system comprising:
(A) a fluid having
a sample containing a target analyte,
first type particles being responsive to a force field, and
second type particles capable of generating a signal,
the first and second type particles having binding moieties such that the first and second type particles link via the target analyte to form a multiple-particle complex;
(B) a cartridge having a capture spot within a fluidic channel, the capture spot including binding moieties for a specific particle defining one of the first and second type particles; and
(C) a force field generator for sequentially moving
a first portion of the fluid responsive to the force field to a location separate from the capture spot,
the first portion to the capture spot such that the at least one multiple-particle complex is captured via the specific particle, and
an uncaptured portion of the first portion away from the capture spot; and
(D) a fluid replacement for removing a second portion of the fluid not responsive to the force field.

2. The system of claim 1, wherein the first type particles are magnetic particles, and wherein the force field generator is a magnet.

3. The system of claim 2, wherein the magnetic particles are polystyrene microspheres including a magnetic component.

4. The system of claim 1, wherein the second type particles are luminescent particles.

5. The system of claim 4, further comprising an excitation source for providing excitation energy so as to illuminate at least a portion part of the fluidic channel, and wherein the second type particles are fluorescent particles configured for generating a fluorescent signal when the excitation energy is incident thereon.

6. The system of claim 5, further including a planar waveguide, wherein the excitation energy is directed into the portion of the fluidic channel at least in part by total internal reflection through the planar waveguide.

7. The system of claim 1, wherein the cartridge includes a plurality of capture spots disposed on a waveguide and within the fluidic channel.

8. A method for sample processing and analyte detection, the method comprising the following sequential steps:
(A) using a force field, moving a first portion of a fluid responsive to the force field to a location separate from a capture spot, the fluid having a sample containing a target analyte, first type particles responsive to the force field, and second type particles capable of generating a signal, the first and second type particles including binding moieties such that the first and second type particles link via the target analyte to form a multiple-particle complex; the capture spot being within a fluidic channel of a cartridge and having binding moieties for a specific particle defining one of the first or second type particles;
(B) using the force field, moving the first portion to the capture spot such that the multiple-particle complex is captured via the specific particle;
(C) manipulating a second portion of the fluid not responsive to the force field to separate the first type particles and the multiple-particle complex from the second type particles, and using the force field, moving an uncaptured portion of the first portion away from the capture spot; and
(D) detecting the multiple-particle complex at the capture spot;
wherein steps (A)-(C) comprise applying a magnetic field to at least a portion of the first and second type particles and the multiple-particle complex.

9. The method of claim 8, wherein the second type particles comprise luminescent molecules.

10. The method of claim 9, wherein the luminescent molecules comprise fluorescent molecules.

11. The method of claim 10, wherein detecting the multiple-particle complex comprises:
illuminating the multiple-particle complex with an excitation energy, and
sensing the signal generated by the second type particles so illuminated.

12. The method of claim 11, wherein illuminating at least some of the multiple-particle complex comprises containing and guiding the excitation energy within a volume such that only the first type particles, second type particles, and multiple-particle complex disposed adjacent to the volume is illuminated.

13. The method of claim 12, wherein, in stein (C), manipulating comprises manipulating the second portion of the fluid away from the volume such that only the first type particles and multiple-particle complex are illuminated.

14. The method of claim 12, wherein the multiple-particle complex exhibits directional signal enhancement, and wherein detecting the multiple-paticle complex comprises sensing the signal in a manner sensitive to the directional signal enhancement.

15. The method of claim 8, wherein using the force field comprises exposing the sample to the force field so as to retain the multiple-particle complexes while removing from the sample the second type particles that are unlinked to the target analyte, the method further comprising
providing an excitation energy to the fluid such that the second type particles, linked in the multiple-particle complexes, generate a detectable signal.

16. The method of claim 8,
the target analyte comprising a first target analyte and a second target analyte;
the first type particles comprising a first-first and a second-first type particles, each of the first-first and second-first type particles capable of binding to a different one of the first and second target analytes and being responsive to the force field;
the multiple particle complex comprising a first multiple particle complex and a second multiple particle complex,
the first multiple particle complex including one of the first-first type particles and one of the second type particles linked via one of the first target analytes,
the second multiple particle complex including one of the second-first type particles and one of the second type particles linked via one of the second plurality of target analytes;
the capture spot comprising
a first capture spot having binding moieties for a first specific particle defining the first-first type particle, and
a second capture spot having binding moieties for a second specific particle defining the second-first type particle;
wherein steps (B) and (C) comprise
moving the first portion to the first capture spot such that the first multiple particle complex is captured via the first specific particle, and then moving a first uncaptured portion of the first portion to the second capture spot such that the second multiple particle complex is captured via the second specific particle.

17. The method of claim 8,
the target analyte comprising a first target analyte and a second target analyte;
the second type particles comprising a first-second and a second-second type particles, each of the first-second and second-second type particles capable of binding to a different one of the first and second target analytes and capable of generating a signal;
the multiple particle complex comprising a first multiple particle complex and a second multiple particle complex,
the first multiple particle complex including one of the first-second type particle and one of the first type particles linked via one of the first target analytes,
the second multiple particle complex including one of the second-second type particle and one of the first type particles linked via one of the second target analytes;
the capture spot comprising
a first capture spot having binding moieties for a first specific particle defining the first-second type particle, and
a second capture spot having binding moieties for a second specific particle defining the second-second type particle;
wherein steps (B) and (C) comprise
moving the first portion to the first capture spot such that the first multiple particle complex is captured via the first specific particle, and
then moving a first uncaptured portion of the first portion to the second capture spot such that the second multiple particle complex is captured via the second specific particle.

18. A system for sample preparation and analyte detection, the system comprising:
(A) a fluid having
a sample containing a target analyte,
first type particles being responsive to a force field, and
second type luminescent particles configured for generating a fluorescent signal when excitation energy is incident thereon,
the first and second type particles having binding moieties such that the first and second type particles link via the target analyte to form a multiple-particle complex;
(B) a cartridge having a capture spot within a fluidic channel, the capture spot including binding moieties for a specific particle defining one of the first and second type particles;
(C) an excitation source for illuminating at least part of the fluidic channel so as to provide the excitation energy;
(D) a planar waveguide, wherein the excitation energy is directed into the portion of the fluidic channel at least in part by total internal reflection through the planar waveguide; and,
(E) a force field generator for sequentially moving
a first portion of the fluid responsive to the force field to a location separate from the capture spot,
the first portion to the capture spot such that the multiple-particle complex is captured via the specific particle, and
an uncaptured portion of the first portion away from the capture spot.

19. A method for sample processing and analyte detection, the method comprising the following sequential steps:
(A) using a force field, moving a first portion of a fluid responsive to the force field to a location separate from a capture spot, the fluid having a sample containing a target analyte, first type particles responsive to the force field, and second type particles capable of generating a signal, the first and second type particles including binding moieties such that the first and second type particles link via the target analyte to form a multiple-particle complex; the capture spot being within a fluidic channel of a cartridge and having binding moieties for a specific particle defining one of the first or second type particles;
(B) using the force field, moving the first portion to the capture spot such that the multiple-particle complex is captured via the specific particle;
(C) using the force field, moving an uncaptured portion of the first portion away from the capture spot;
(D) using the force field to retain the multiple-particle complex while removing from the sample the second type particles that are unlinked to the target analyte;
(E) providing an excitation energy to the fluid such that the second type particle, linked in the multiple-particle complex, generates a detectable signal; and
(F) detecting the multiple-particle complex at the capture spot.

20. A method for sample processing and analyte detection, the method comprising the following sequential steps:
(A) using a force field, moving a first portion of a fluid responsive to the force field to a location separate from a capture spot, the fluid having a sample containing a target analyte, first type particles responsive to the force field, and second type particles comprising fluorescent molecules capable of generating a signal, the first and second type particles including binding moieties such that the first and second type particles link via the target analyte to form a multiple-particle complex; the capture spot being within a fluidic channel of a cartridge and having binding moieties for a specific particle defining one of the first or second type particles;
(B) using the force field, moving the first portion to the capture spot such that the multiple-particle complex is captured via the specific particle;
(C) using the force field, moving an uncaptured portion of the first portion away from the capture spot;
(D) illuminating the multiple-particle complex with an excitation energy and sensing the signal generated by the second type particles so illuminated so as to detect the multiple-particle complex at the capture spot; illuminating comprising containing and guiding the excitation energy within a volume such that only the first type particles, second type particles, and multiple-particle complex disposed adjacent to the volume are illuminated; and
(E) manipulating a second portion of the fluid not responsive to the force field away from the volume such that only the first type particles and multiple-particle complex are illuminated.

21. A method for sample processing and analyte detection, the method comprising the following sequential steps:
(A) using a force field, moving a first portion of a fluid responsive to the force field to a location separate from a capture spot, the fluid having a sample containing a target analyte, first type particles responsive to the force field, and second type particles comprising fluorescent molecules capable of generating a signal, the first and second type particles including binding moieties such that the first and second type particles link via the target analyte to form a multiple-particle complex; the capture spot being within a fluidic channel of a cartridge and having binding moieties for a specific particle defining one of the first or second type particles;
(B) using the force field, moving the first portion to the capture spot such that the multiple-particle complex is captured via the specific particle;
(C) using the force field, moving an uncaptured portion of the first portion away from the capture spot;
(D) illuminating the multiple-particle complex with an excitation energy and sensing the signal generated by the second type particles so illuminated so as to detect the multiple-particle complex at the capture spot; illuminating comprising containing and guiding the excitation energy within a volume such that only the first type particles, second type particles, and multiple-particle complex disposed adjacent to the volume are illuminated; detecting the multiple-particle complex comprising sensing the signal in a manner sensitive to directional signal enhancement exhibited by the multiple particle complex.

22. A system for sample preparation and analyte detection, the system comprising:

(A) a fluid having
a sample containing a target analyte,
first type particles being responsive to a force field, and
second type particles capable of generating a signal,
the first and second type particles having binding moieties such that the first and second type particles link via the target analyte to form a multiple-particle complex;
(B) a cartridge having a capture spot disposed on a waveguide and within a fluidic channel, the capture spot including binding moieties for a specific particle defining one of the first and second type particles; and
(C) a force field generator for sequentially moving
(i) a first portion of the fluid responsive to the force field to a location separate from the capture spot,
(ii) the first portion to the capture spot such that the multiple-particle complex is captured via the specific particle, and
(iii) an uncaptured portion of the first portion away from the capture spot.

* * * * *

UNITED STATES PATENT AND TRADEMARK OFFICE
CERTIFICATE OF CORRECTION

PATENT NO.         : 8,697,435 B2                                     Page 1 of 1
APPLICATION NO.    : 12/871402
DATED              : April 15, 2014
INVENTOR(S)        : Heil et al.

It is certified that error appears in the above-identified patent and that said Letters Patent is hereby corrected as shown below:

In the Claims:

Column 38, Line 23, "in stein" should read --in step--.

Signed and Sealed this
Twenty-sixth Day of August, 2014

Michelle K. Lee
*Deputy Director of the United States Patent and Trademark Office*

SEQUENCE LISTING

<160> NUMBER OF SEQ ID NOS: 23

<210> SEQ ID NO 1
<211> LENGTH: 100
<212> TYPE: DNA
<213> ORGANISM: Influenza A H1N1 Virus

<400> SEQUENCE: 1
tccaacgtga agaatctgta tgagaaagta aaaagccaat taaagaataa tgccaaagaa 60
ataggaaacg ggtgttttga attctatcac aagtgtaacg 100

<210> SEQ ID NO 2
<211> LENGTH: 62
<212> TYPE: DNA
<213> ORGANISM: Influenza A H1N1 Virus
<220> FEATURE:
<221> NAME/KEY: misc_feature
<222> LOCATION: (2)..(2)
<223> OTHER INFORMATION: n is a, c, g, or t

<400> SEQUENCE: 2
cnhttttttt ttcgttacac ttgtgataga attcaaaaca cccgtttcct atttctttgg 60
ca 62

<210> SEQ ID NO 3
<211> LENGTH: 48
<212> TYPE: DNA
<213> ORGANISM: Influenza A H1N1 Virus
<220> FEATURE:
<221> NAME/KEY: misc_feature
<222> LOCATION: (47)..(47)
<223> OTHER INFORMATION: n is a, c, g, or t

<400> SEQUENCE: 3
tttaattggc tttttacttt ctcatacaga ttcttcacgt tggatcnh 48

<210> SEQ ID NO 4
<211> LENGTH: 61
<212> TYPE: RNA

```
<213> ORGANISM: Influenza A H1N1 Virus

<400> SEQUENCE: 4
ugcaggacuu ucuuucuaac ucaaggggcc uuguugaaug acaagcauuc caauggaacc    60
g                                                                   61

<210> SEQ ID NO 5
<211> LENGTH: 59
<212> TYPE: DNA
<213> ORGANISM: Influenza A H1N1 Virus

<400> SEQUENCE: 5
tttttttttc gttacacttg tgatagaatt caaaacaccc gtttcctatt tctttggca    59

<210> SEQ ID NO 6
<211> LENGTH: 44
<212> TYPE: DNA
<213> ORGANISM: Influenza A H1N1 Virus
<220> FEATURE:
<221> NAME/KEY: misc_feature
<222> LOCATION: (43)..(43)
<223> OTHER INFORMATION: n is a, c, g, or t

<400> SEQUENCE: 6
ggccccttga gttagaaaga aagtcctgca ttttttttt tcnh                      44

<210> SEQ ID NO 7
<211> LENGTH: 41
<212> TYPE: DNA
<213> ORGANISM: Influenza A H1N1 Virus

<400> SEQUENCE: 7
ggccccttga gttagaaaga aagtcctgca ttttttttt t                         41

<210> SEQ ID NO 8
<211> LENGTH: 47
<212> TYPE: DNA
<213> ORGANISM: Influenza A H1N1 Virus
<220> FEATURE:
<221> NAME/KEY: misc_feature
<222> LOCATION: (46)..(46)
<223> OTHER INFORMATION: n is a, c, g, or t

<400> SEQUENCE: 8
ccaacgtgaa gaatctgtat gagaaagtaa aaagtttttt tttcnh                   47

<210> SEQ ID NO 9
<211> LENGTH: 37
<212> TYPE: DNA
<213> ORGANISM: Influenza A H1N1 Virus
<220> FEATURE:
<221> NAME/KEY: misc_feature
<222> LOCATION: (36)..(36)
<223> OTHER INFORMATION: n is a, c, g, or t

<400> SEQUENCE: 9
gaaaatacaa caatctggac tagtgttttt ttttcnh                             37

<210> SEQ ID NO 10
<211> LENGTH: 36
<212> TYPE: DNA
<213> ORGANISM: Influenza A H3N2 Virus
<220> FEATURE:
<221> NAME/KEY: misc_feature
<222> LOCATION: (35)..(35)
<223> OTHER INFORMATION: n is a, c, g, or t
```

```
<400> SEQUENCE: 10
cctggagaac caacatacaa ttgattttttt tttcnh                              36

<210> SEQ ID NO 11
<211> LENGTH: 43
<212> TYPE: DNA
<213> ORGANISM: Influenza A H3N2 Virus
<220> FEATURE:
<221> NAME/KEY: misc_feature
<222> LOCATION: (42)..(42)
<223> OTHER INFORMATION: n is a, c, g, or t

<400> SEQUENCE: 11
tcatggagtg aaaggctggg cctttgatga ttttttttt cnh                        43

<210> SEQ ID NO 12
<211> LENGTH: 42
<212> TYPE: DNA
<213> ORGANISM: Influenza A H1N1 Virus
<220> FEATURE:
<221> NAME/KEY: misc_feature
<222> LOCATION: (2)..(2)
<223> OTHER INFORMATION: n is a, c, g, or t

<400> SEQUENCE: 12
cnhttttttt tttgttgaat gacaagcatt ccaatggaac cg                        42

<210> SEQ ID NO 13
<211> LENGTH: 18
<212> TYPE: DNA
<213> ORGANISM: Francisella tularensis

<400> SEQUENCE: 13 gccacctta atccacag                                                    18

<210> SEQ ID NO 14
<211> LENGTH: 19
<212> TYPE: DNA
<213> ORGANISM: Random DNA Sequence

<400> SEQUENCE: 14
attcgtggca agttctcag                                                  19

<210> SEQ ID NO 15
<211> LENGTH: 45
<212> TYPE: DNA
<213> ORGANISM: Influenza A H1N1 Virus

<400> SEQUENCE: 15
tttaattggc tttttacttt ctcatacaga ttcttcacgt tggat                     45

<210> SEQ ID NO 16
<211> LENGTH: 34
<212> TYPE: DNA
<213> ORGANISM: Influenza A H1N1 Virus

<400> SEQUENCE: 16
cactagtcca gattgttgta ttttcttttt tttt                                 34

<210> SEQ ID NO 17
<211> LENGTH: 33
<212> TYPE: DNA
<213> ORGANISM: Influenza A H3N2 Virus

<400> SEQUENCE: 17
```

-continued tcaattgtat gttggttctc caggtttttt ttt                                    33

<210> SEQ ID NO 18
<211> LENGTH: 40
<212> TYPE: DNA
<213> ORGANISM: Influenza A H3N2 Virus

<400> SEQUENCE: 18
atcatcaaag gcccagcctt tcactccatg atttttttt                              40

<210> SEQ ID NO 19
<211> LENGTH: 39
<212> TYPE: DNA
<213> ORGANISM: Influenza A H1N1 Virus

<400> SEQUENCE: 19
tttttttttc ctatttcttt ggcattattc tttaattgg                              39

<210> SEQ ID NO 20
<211> LENGTH: 34
<212> TYPE: DNA
<213> ORGANISM: Influenza A H1N1 Virus

<400> SEQUENCE: 20 tttttttta cgccacaaaa agaaatgctg ctcc                                    34

<210> SEQ ID NO 21
<211> LENGTH: 39
<212> TYPE: DNA
<213> ORGANISM: Influenza A H3N2 Virus

<400> SEQUENCE: 21 tttttttta acagtttgtt catttctgag tcagttaga                               39

<210> SEQ ID NO 22
<211> LENGTH: 38
<212> TYPE: DNA
<213> ORGANISM: Influenza A H3N2 Virus

<400> SEQUENCE: 22 tttttttta tcgttcttcc catccacacg tcatttcc                                38

<210> SEQ ID NO 23
<211> LENGTH: 100
<212> TYPE: DNA
<213> ORGANISM: Influenza A H1N1 Virus

<400> SEQUENCE: 23
tccaacgtga agaatctgta tgagaaagta aaaagccaat taaagaataa tgccaaagaa       60
ataggaaacg ggtgttttga attctatcac aagtgtaacg                            100